(12) United States Patent
Cole et al.

(10) Patent No.: US 6,761,722 B2
(45) Date of Patent: Jul. 13, 2004

(54) TISSUE ANCHORING SYSTEM AND METHOD

(75) Inventors: J. Dean Cole, Orlando, FL (US); Daniel F. Justin, Logan, UT (US)

(73) Assignee: Orthodyne, Inc., Orlando, FL (US)

( * ) Notice: Subject to any disclaimer, the term of this patent is extended or adjusted under 35 U.S.C. 154(b) by 212 days.

(21) Appl. No.: 10/068,115

(22) Filed: Feb. 5, 2002

(65) Prior Publication Data

US 2002/0091391 A1 Jul. 11, 2002

Related U.S. Application Data

(62) Division of application No. 09/560,293, filed on Apr. 27, 2000, now Pat. No. 6,544,267, which is a division of application No. 09/013,434, filed on Jan. 26, 1998, now Pat. No. 6,068,648.

(51) Int. Cl.[7] .............................................. A61B 17/04
(52) U.S. Cl. ........................... 606/74; 606/232; 606/57
(58) Field of Search .............................. 606/232, 153, 606/155, 57

(56) References Cited

U.S. PATENT DOCUMENTS

| | | |
|---|---|---|
| 2,485,531 A | 10/1949 | Dzus et al. |
| 3,513,848 A | 5/1970 | Winston et al. |
| 3,931,667 A | 1/1976 | Merser et al. |
| 4,535,764 A | 8/1985 | Ebert |
| 4,653,309 A | 3/1987 | Hendricks et al. |
| 4,688,561 A | 8/1987 | Reese |
| 4,738,255 A | 4/1988 | Goble et al. ................. 606/232 |
| 4,741,330 A | 5/1988 | Hayhurst .................... 606/232 |
| 4,796,612 A | 1/1989 | Reese ......................... 606/232 |
| 4,889,110 A | 12/1989 | Galline et al. ............... 606/232 |
| 5,041,129 A | 8/1991 | Hayhurst et al. ............ 606/232 |
| 5,098,433 A | 3/1992 | Freedland .................... 606/232 |
| 5,102,421 A | 4/1992 | Anspach, Jr. ................ 606/232 |
| 5,108,433 A | 4/1992 | May et al. |
| 5,116,340 A | 5/1992 | Songer et al. |
| 5,250,049 A | 10/1993 | Michael |
| 5,306,301 A | 4/1994 | Graf et al. |
| 5,312,410 A | 5/1994 | Miller et al. |
| 5,318,566 A | 6/1994 | Miller |
| 5,395,374 A | 3/1995 | Miller et al. |
| 5,405,359 A | 4/1995 | Pierce |
| 5,417,700 A | 5/1995 | Egan |
| 5,449,361 A | 9/1995 | Preissman |
| 5,505,733 A | 4/1996 | Justin et al. |
| 5,505,735 A | 4/1996 | Li ............................... 606/232 |
| 5,536,270 A | 7/1996 | Songer et al. |
| 5,601,557 A | 2/1997 | Hayhurst ..................... 606/232 |
| 5,645,588 A | 7/1997 | Graf et al. |
| 5,772,663 A | 6/1998 | Whiteside et al. |
| 5,879,357 A | 3/1999 | Heaton et al. |
| 6,117,160 A | * 9/2000 | Bonutti ........................ 606/215 |

FOREIGN PATENT DOCUMENTS

EP         464480         1/1992

* cited by examiner

*Primary Examiner*—Gary Jackson
(74) *Attorney, Agent, or Firm*—Haynes and Boone, LLP

(57) ABSTRACT

A tissue anchoring system includes a tissue anchor affixed to an end of a cable and supported for insertion on a delivery device, the manipulation of which permits placement of the anchor on a far side of the tissue. A tensioning, crimping and cutting tool designed for use along the cable's longitudinal axis, thus reducing the number of incisions required. A suture anchoring system is also described for introducing a loop of suture into a surgical site and anchoring it, for instance, across a tear in soft tissue.

21 Claims, 17 Drawing Sheets

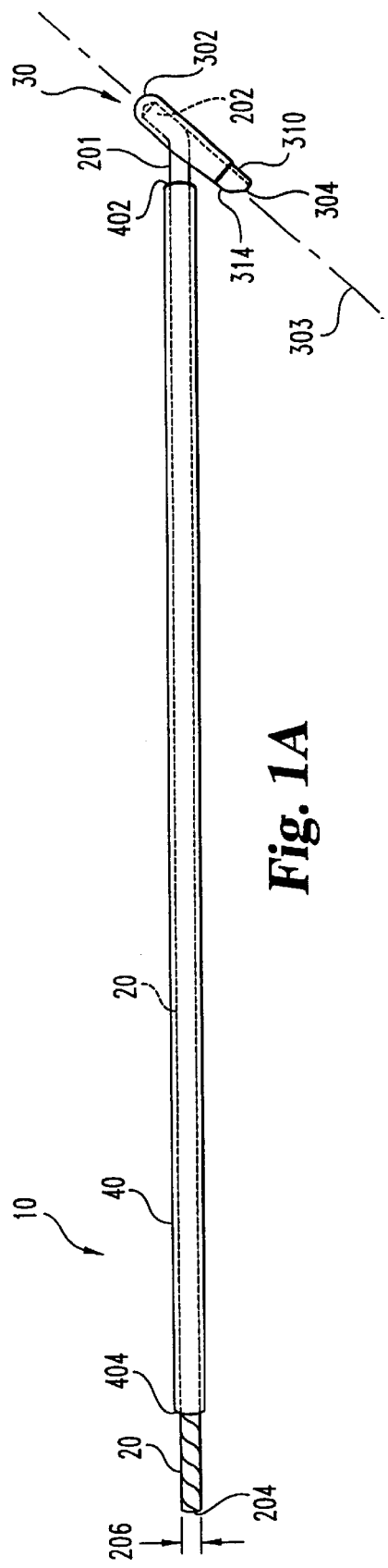
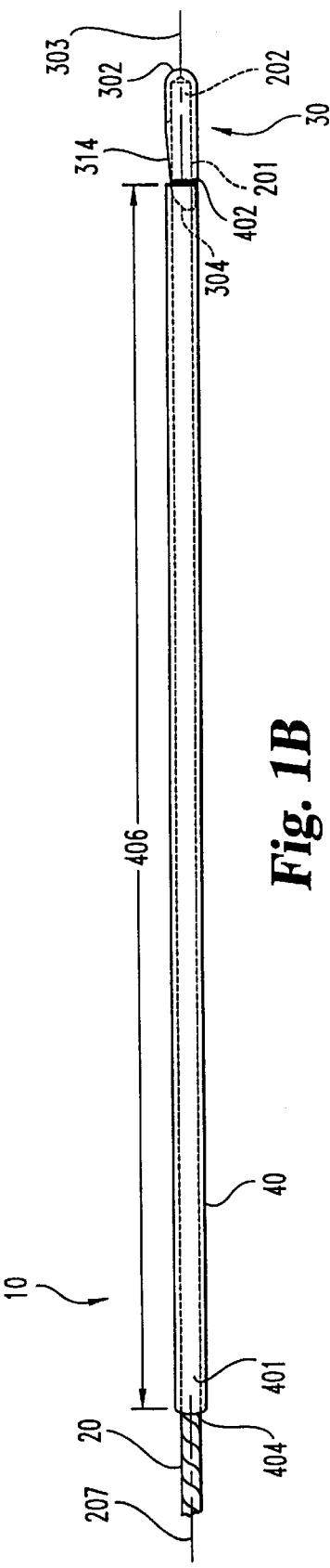

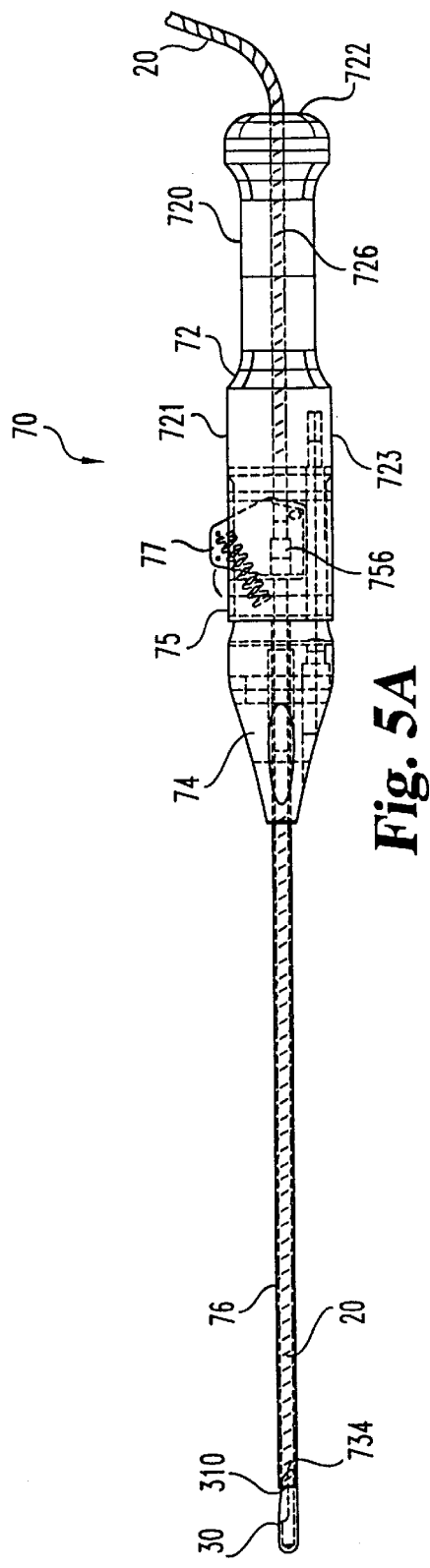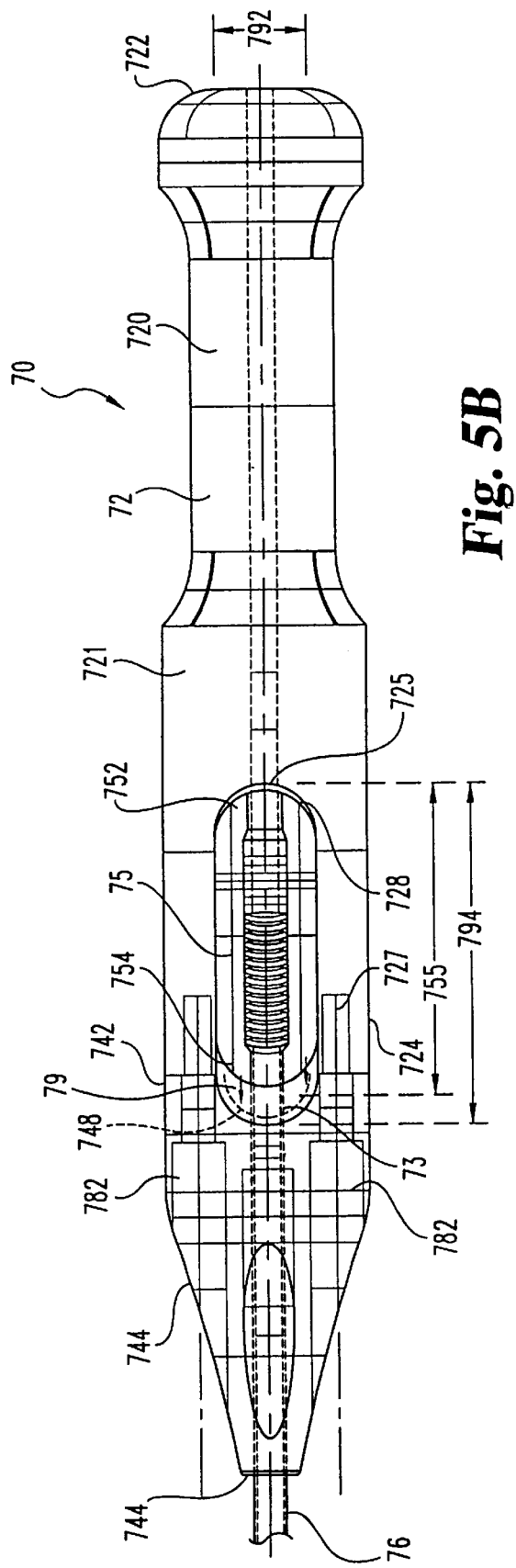
Fig. 5A
Fig. 5B

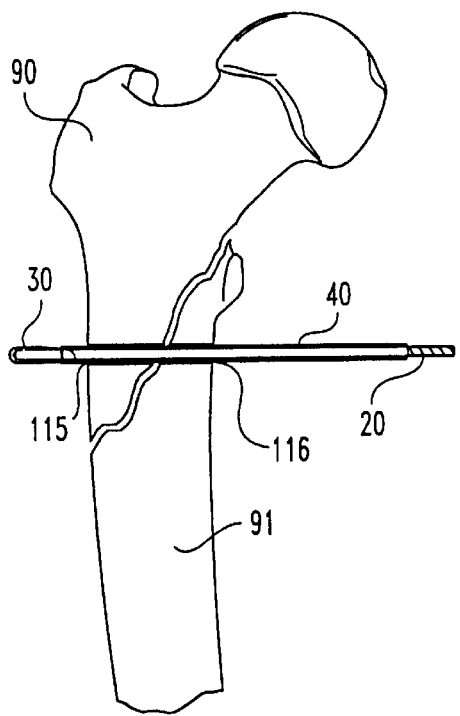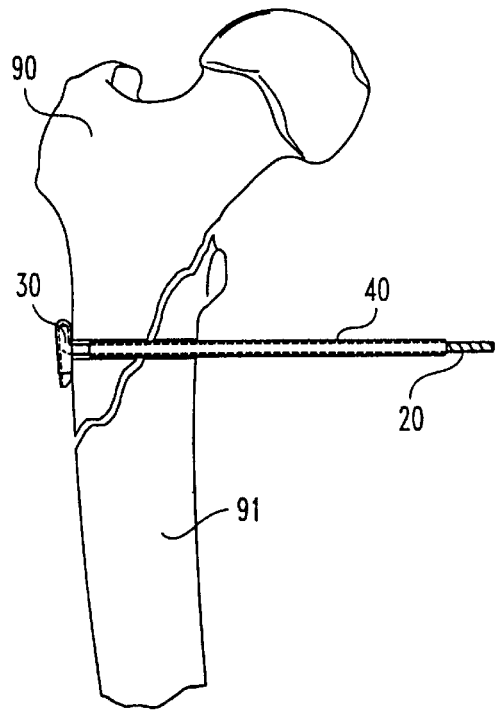
*Fig. 12A*  *Fig. 12B*
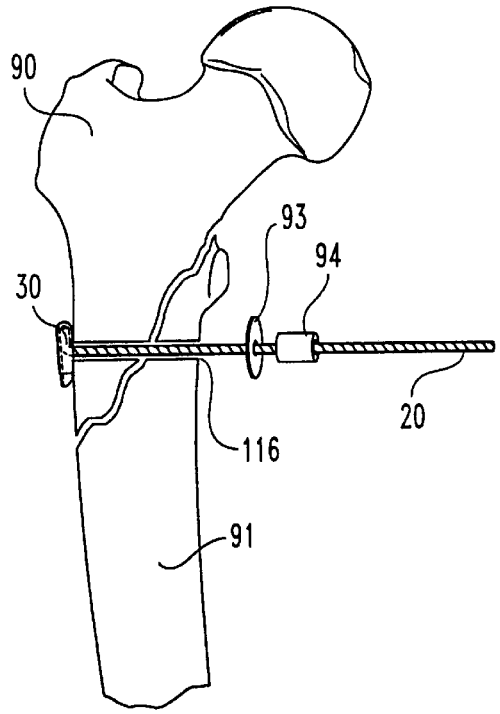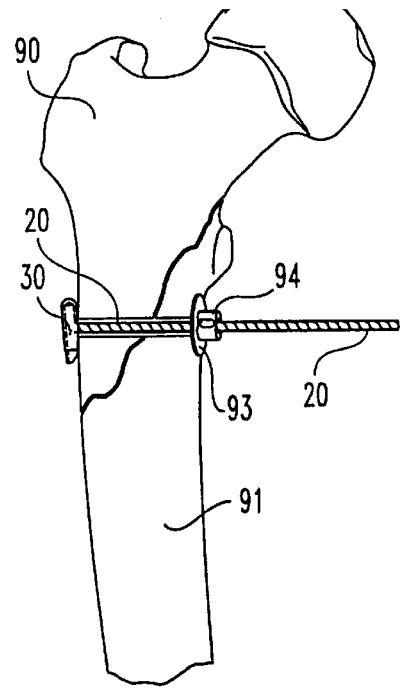
*Fig. 12C*  *Fig. 12E*

TISSUE ANCHORING SYSTEM AND METHOD

This application claims the benefit of U.S. patent application Ser. No. 09/560,293 filed Apr. 27, 2000, now U.S. Pat. No. 6,544,267 granted Apr. 8, 2003; which is a Divisional of U.S. patent application Ser. No. 09/013,434 filed Jan. 26, 1998 now U.S. Pat. No. 6,068,648 granted May 30, 2000.

BACKGROUND OF THE INVENTION

The present invention relates to surgical devices and methods and, more particularly, to devices and methods for the repair of bone and soft tissue.

It is a common requirement in orthopedic surgical procedures to anchor two or more elements together, such as pieces of a bone, two or bones, or a combination of soft tissue and bone. This has been accomplished by a number of devices, such as bone bolts that penetrate two pieces of bone and use a nut to draw the segments together, bone screws and interconnecting plates, wires circling at least two pieces of bone, or sutures into the tissue.

Often such devices require a relatively large access opening through surrounding and/or covering tissue to implant the anchoring devices. The enlarged access site may increase patient pain and lengthen recovery time. Further, in some locations it is difficult and impractical to make large access points to reach the appropriate site because of surrounding joints and vessels. Even with devices that penetrate the tissue in a substantially linear manner, i.e. lag bolts, the fracture must often be reduced before drilling and insertion of the bolt. Further, some of these devices may be difficult to use since it may be hard to reduce a fracture between two bone segments and maintain that reduction while the device is inserted. This is particularly true with small bone fragments where the use of threaded implants may tend to rotate one bone segment with respect to another, thereby creating a misalignment between the fragments.

Cerclage systems provide an alternative to implants that must penetrate the bone to achieve fixation. Such devices have been taught by Miller et al. (U.S. Pat. No. 5,312,410) and Songer et al. (U.S. Pat. No. 5,536,270). These systems rely on passing a cable around two segments of bone and then tensioning the cable to squeeze the bone segments together. A significant drawback of these systems is that they require access around the entire bone.

Therefore, there remains a need for a convenient and effective system for securing two segments of tissue together. Such a system should preferably be operable through a relatively small insertion opening or openings to securely hold two tissue segments.

SUMMARY OF THE INVENTION

An anchor system according to the present invention can comprise an elongated flexible member having a diameter, a proximal end, a distal end and a longitudinal axis; an anchor having a proximal end, a distal end, a central portion between the proximal end and the distal end and a longitudinal axis extending between the proximal end and the distal end, the anchor including a longitudinal slot extending longitudinally from the proximal end to the central portion, the slot having a width greater than the flexible member diameter, the flexible member distal end affixed adjacent the central portion. The anchor is moveable relative to the flexible member between a first position wherein the longitudinal axes of the flexible member and the anchor are generally parallel with a portion of the flexible member adjacent the distal end residing within the slot and a second position wherein the longitudinal axes of the flexible member and the anchor are generally perpendicular.

Another embodiment of an anchoring system according to the present invention, comprises an elongated flexible member having a proximal end, a distal end and a first diameter; and an anchor affixed to the distal end, the anchor moveable between an insertion configuration adapted for insertion through a tissue opening and an anchoring configuration adapted to inhibit passage through the tissue opening, the insertion configuration having a second diameter less than twice the first diameter, and the anchoring configuration having a third diameter greater than the second diameter.

The system further includes a delivery device having a distal end, the distal end adapted to releasably receive at least the anchor proximal end for releasably retaining the anchor in the first position for insertion through at least a portion of a section of tissue, the anchor releasable from the delivery device for anchoring the flexible member in the section of tissue. The delivery device includes a mechanism for releasably exerting a longitudinal force on the flexible member in a proximal direction, for retaining the anchor proximal end in the delivery device and thereby in the first position.

In one embodiment, the insertion device comprises an inner tube having a longitudinal bore extending from a proximal end to a distal end, the inner bore sized to permit passage of an elongated flexible member and to prevent passage of an anchor attached to an elongated flexible member; an outer tube having a longitudinal bore extending from a proximal end to a distal end, the outer tube bore dimensioned to permit the inner tube to pass therethrough; and a mechanism for applying tension to an elongated flexible member, the means positioned adjacent the distal end of the inner tube.

The system of the present invention further contemplates a crimping tool which can comprise an outer member having an inner passage and a distal end having an outer diameter. A crimping mechanism can be disposed within the inner passage adjacent the distal end. The crimping mechanism movable with respect to the outer member between a crimping position and an open position.

An alternative embodiment of the present invention includes a suture anchoring system for attaching a first section of tissue to a second section of tissue via a unitary incision having a longitudinal axis. The anchoring system comprises a suture anchor connected to a suture material having a first end, a second end, a longitudinal axis, and a diameter. The suture anchor has a longitudinal axis generally extending from a proximal end to a distal end and a first cross-sectional dimension generally along the longitudinal axis greater than a second cross-sectional dimension generally perpendicular to the longitudinal axis. The system further includes a mechanism for slidably affixing a central portion of the suture material to the suture anchor, the first end and the second end of the suture material retainable outside the incision. The suture anchor is pivotable relative to the suture material between a first position wherein the longitudinal axes of the incision and the suture anchor are generally parallel and a second position wherein the longitudinal axes of the incision and the suture anchor are generally perpendicular.

The present invention also contemplates a bone opening protector having a first portion defining an opening therein to receive a cable. The first portion is adapted to engage a surface surrounding a bone opening. The protector also includes an anchoring extension, connected to the first portion, adapted to extend into bone to inhibit movement of the first portion.

The invention further contemplates a method for joining two sections of tissue. The method includes providing a first anchor, an elongated member attached to the first anchor, a second anchor slidable on the elongated member and having a deformable portion adapted to engage the elongated member, and a crimping tool having an outer member and an inner member movably disposed within the outer member. The first anchor is inserted into a first section of tissue. The second anchor is threaded on the elongated member. Tension is applied on the elongated member to urge the first section of tissue toward a second section of tissue. The elongated member is threaded through the crimping device, and the inner member of the crimping device is moved with respect to the outer member thereby deforming the deformable portion of the second anchor and maintaining the tension applied to the elongated member.

One object of the invention is to provide an element for anchoring tissue.

Another object is to provide a system for delivering the tissue anchoring element.

A further object is to provide such a system that also tightens and ligates the anchoring element.

An additional object of the present invention is to provide a crimping tool.

Still another object is to provide a method for delivering a tissue anchoring element to a surgical site.

Yet another object is to provide an element for anchoring suture material.

Yet a further object is to provide a system for delivering the suture anchoring element.

Yet an additional object is to provide a method for delivering a suture anchoring element to a surgical site.

Still a further object of the present invention is to provide a bone opening protector.

Other objects and advantages of the present invention will be apparent from the following description.

BRIEF DESCRIPTION OF THE DRAWINGS

FIG. 1A is a perspective side view of the cable/anchor element of the present invention in an anchor position, ready to anchor tissue.

FIG. 1B is a perspective side view of the cable/anchor element of the present invention in an insertion position, ready for delivery by the delivery device.

FIG. 5A is a side partial cross-sectional view of the delivery device of FIG. 4.

FIG. 5B is a top partial cross-sectional view of the delivery device of FIG. 5A.

DESCRIPTION OF THE PREFERRED EMBODIMENTS

Figure 2A:
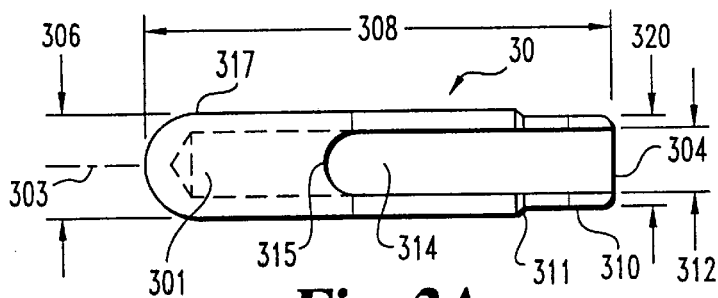
FIG. 2A is a top view of the anchor of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device; and such further applications of the principles of the invention as illustrated therein being contemplated as would normally occur to one skilled in the art to which the invention relates.

Referring to FIG. 1A, a tissue anchoring system 10 according to the present invention includes a cable 20 having an anchor 30 affixed to a distal end 202. A delivery device 40 is also provided for aiding in inserting the cable 20 through tissue. The term "tissue" is used herein to include any manner of body part including without limitation, bone, cartilage, ligaments, tendons, and muscle.

Referring to FIG. 1A, cable 20 may be any elongated flexible member, the choice of material and size being dependent upon the particular application. For the purposes of illustration and without limitation, the flexible member is referred to and shown as a cable, although it is within the spirit of the invention that a flexible member could similarly be a filament, thread, suture, wire, substantially flat ribbon type member, or any other flexible member suitable for implantation in the body. Cable 20 may comprise such biocompatible materials as stainless steel, titanium, nitinol, plastic, bioresorbable material, composite material, or cobalt chrome alloy. The list of possible cable compositions is provided for the purpose of illustration and is not intended as limiting, it being understood that selection of a cable may depend on the intended application. In a preferred embodiment for use in bone fracture reductions, cable 20 is a flexible multistranded metallic cable such as stainless steel as is already known in the art. In a system for affixing two sections of soft tissue together, suture material or an equivalent threadlike material can be used instead of metallic cable. Thus, it is to be assumed herein that the word "cable" should be taken to mean any flexible material that can be used in surgical applications for affixing two sections of tissue together, and no limitations are intended thereby.

Cable Anchor

Attached to the cable's distal end 202 is a generally cylindrical anchor 30 (FIGS. 2A and 2B) that has a closed distal end 302, an open proximal end 304, and a partial bore 301 extending from the proximal end 304 but not through to the distal end 302. The distal end 302 is rounded to limit damage to surrounding tissue and for ease of insertion through the tissue to be anchored. Anchor 30 includes a longitudinal axis 303 that extends from the proximal end 304 to the distal end 302. The anchor may be constructed of a material similar to the cable or the anchor may differ from the cable. In one combination, the cable is non-resorbable while the anchor is bioresorbable such that the cable may be removed after a healing period and the anchor may remain in the body.

The anchor 30 has a distal portion 317 having a first cross-sectional diameter 306, or width, larger than the diameter 206 of the cable 20. In a preferred embodiment, diameter 306 is less than twice diameter 206, thus providing a relatively small insertion diameter. This first cross-sectional diameter 306 generally coincides with a cylindrical diameter. In a preferred embodiment, diameter 306 substantially equals the outer diameter of delivery device 40. A second cross-sectional dimension 308, or length, is significantly larger than the width 306. This length 308 generally coincides with the length of the anchor 30 from proximal end 304 to distal end 302.

The anchor 30 also has a proximal portion 310 opposite the distal portion 317, the proximal portion 310 having a width 320, the proximal portion width 320 smaller than the distal portion width 306. The proximal portion 310 includes a taper 318 tapering toward the proximal end 304 and a thickness 322. It will be understood that upon engaging a surface with cable 20 proximally tensioned, taper 318 assists the anchor in flipping to an anchoring position and in sliding under adjacent tissue during the flipping process. There is a shoulder 311 between the proximal portion 310 and the wider distal portion 317, for engaging the distal end of the delivery device 40.

In addition, the anchor 30 has a generally longitudinal slot 314 extending from the proximal end 304 into the distal portion 317. Slot 314 has a width 312 equal to or greater than the cable diameter 206. The distal end 202 of the cable 20 is affixed, for example, via crimping, within the anchor bore 301 between the anchor's distal end 302 and the slot's distal end 315 (see FIG. 1A). In a preferred embodiment, a four point crimp is applied to anchor 302 to secure cable 20 within bore 301. However, it is contemplated that an alternative crimping procedure could be performed as well as welding, brazing, adhesive, etc. Additionally, cable 20 may include a loop at its distal end for attachment through an aperture in the anchor. Any attachment means may be used provided the cable is secured to the anchor with sufficient strength for the intended application.

In a preferred embodiment, the anchor outer diameter 306 is less than twice the cable diameter 206. This permits the cable and anchor combination to be inserted through a relatively small hole or incision. However, the length 308 is much greater than the anchor diameter 306 thereby providing a secure anchorage for the cable.

The anchor 30 is movable in relation to the cable 20 between two positions: a first position (FIG. 1B) wherein the anchor's longitudinal axis 303 is generally parallel to the cable's longitudinal axis 207 and the cable's distal portion 201 resides within anchor slot 314, and a second position (FIG. 1A) wherein the anchor's longitudinal axis 303 is at an angle to the cable's longitudinal axis 206 and a part of the cable's distal portion 201 extends outside anchor slot 314. Anchor 30 includes a curved surface 324 adjacent slot 314 for the cable to bear against and limit abrasion when in the second position. By the nature of the cable-anchor connection, the anchor 30 is biased to the second position. This biasing occurs because the first position is unstable. Such biasing may be induced by a pre-set curve in distal portion 201 of cable 20 positioned within slot 314 tending to rotate anchor 30 to the second position. In addition to biasing the anchor towards the second position, taper 318 on the proximal end of anchor 30 urges rotation of the anchor to the second position when it contacts a surface.

Figure 3A:
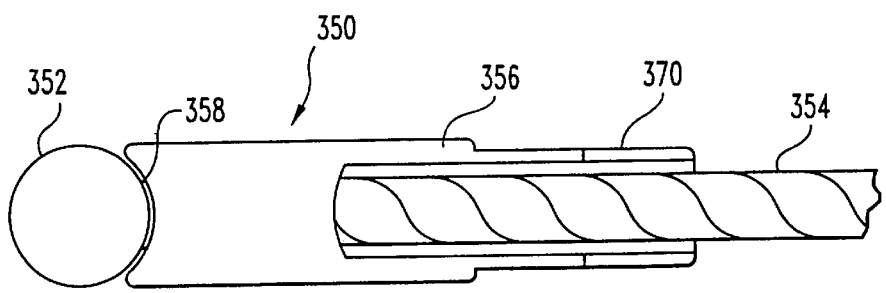
FIG. 3A is a top view of an alternative embodiment of the anchor of the present invention.
Figure 3B:
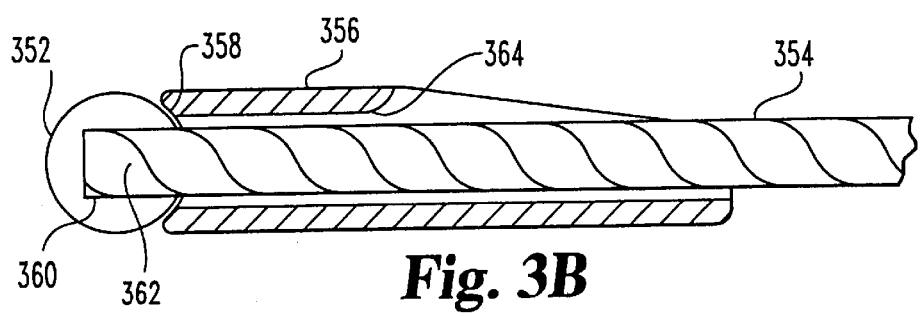
FIG. 3B is a side cross-sectional view of the anchor of FIG. 3A.

FIGS. 3A and 3B show an alternative embodiment of the anchor according to the present invention. The anchor 350 includes a bead 352 having a bore 360 defined therein. The distal end 362 of cable 354 is received within the bore and bead 352 is affixed to the cable. Pivoting member 356 includes a longitudinal slot 370 in communication with a longitudinal bore 364 extending to distal end 358. The bore 364 and slot 370 are sized to slidably receive cable 354 therein. The distal end 358 defines a spherical cavity for receiving a portion of bead 352. Anchor 350 is pivotable from the first insertion position shown in FIGS. 3A and 3B to an anchoring position as shown in FIG. 1A.

Delivery Device

The present invention further contemplates a delivery device for insertion of a cable and anchor combination. Although the device is illustrated for use with the above described anchor, it is contemplated that the delivery device may be used or adapted for use with a variety of cable and anchor combinations. A first embodiment of the delivery device 40 (FIGS. 1 and 2) comprises a rigid metallic cylindrical member having a length 405 sufficient to penetrate a desired surgical site and a longitudinal bore 401 extending from a proximal end 404 to a distal end 402. The bore 401 is sufficiently large to permit the anchor's proximal portion 310 to fit thereinto but too small to permit the anchor's distal portion 317 to fit thereinto. Although a preferred embodiment of the delivery device has the distal portion of anchor 30 extending distally beyond the distal end of the delivery device, it is contemplated that anchor 30 could be entirely retained within the delivery device until it is deployed. In this embodiment (not shown), cable 20 could be fixed with respect to delivery device 40 to prevent accidental deployment of the anchor.

The cable/anchor 20/30 combination is inserted into tissue with the aid of the delivery device 40, which is used to provide mechanical stiffness to the cable 20. The cable's proximal end 204 is passed through the delivery device 40 from the distal end 402 through the bore 401 to beyond the proximal end 404. The anchor's proximal portion 310 is seated in the delivery device bore 401 adjacent the distal end 402, and tension is maintained on the cable's proximal end 204 to retain the anchor 30 in the first position. Although a preferred embodiment of the device shows proximal end 304 held within bore 401, it is contemplated that proximal end 304 may include threads and delivery device 40 may similarly have cooperable threads on the distal end such that the device may be threadedly held on delivery device 40. Alternatively, there may be a frangible connection between proximal end 304 and the distal end of the delivery device, the frangible connection breakable to permit anchor 30 to move to the second position.

In a second embodiment of a delivery device according to the present invention,(FIGS. 4, 5A, and 5B), the impelling means comprises means for releasably maintaining a longitudinal force on cable 20 in a proximal direction, for retaining the anchor 30 in the first position.

In this embodiment, the delivery device 70 comprises a body 72, which has a handle portion 720 having a proximal end 722 and a recess 728 at the distal end 724. The recess 728, which extends from the top 721 to the bottom 723 of the delivery device body 72, is rounded at its proximal end 725. A longitudinal bore 726 extends from the proximal end 722 to the distal 724 end, the bore 726 being dimensioned to permit cable 20 to pass therethrough.

A pawl housing 75 is movably affixed to the delivery device body's distal end 724 via its rounded proximal side 752, which is dimensioned to slide longitudinally within the delivery device body's recess 728. The pawl housing 75 has a pawl cavity 758 that extends from the pawl housing's top 751 through a portion of the pawl housing. The pawl housing 75 additionally has a longitudinal bore 756 that extends from the proximal side 752 to the distal side 754 through the pawl cavity 758. The bore 756 is dimensioned to permit cable 20 to pass therethrough, and is adapted for communication with the delivery device body's bore 726 when the device is assembled for use. A spring bore 757 extends from the distal side 754 into the pawl cavity 758 and is positioned above the longitudinal bore 756.

The delivery device 70 further comprises an inner tube 73 that is affixed at its proximal end 732 to the pawl housing's distal side 754. The inner tube 73 is generally cylindrical and has a longitudinal bore 736 that extends from the proximal end 732 to the distal end 734 and is dimensioned to permit the cable 20 to pass therethrough but is too small at the distal end 734 to permit the anchor's proximal portion 310 to enter. This bore 736 is in communication with the pawl housing bore 756.

Another element of the delivery device 70 is a nose assembly 74 that is in mechanical communication with the pawl housing 75. The proximal side 742 is affixed to the distal end 724 of the delivery device body 72 with two screws (not shown). These screws are inserted through first and second screw bores 782 that extend from the tapered distal side 744 of the nose assembly 74 through to the proximal side 742. First and second screw bores 782 are positioned to meet third and fourth screw bores 727 (FIG. 10B) that extend into the body 72 from the body's distal end 724.

The nose assembly 74 has a rounded recess 748 that extends from the top 741 to the bottom 743 and is shaped to receive the rounded distal side 754 of the pawl housing 75. The two recesses 748,728 together define an enclosed elongated hole 79 that has a width 792 dimensioned to closely and slidably engage the pawl housing 75 and a length 794 greater than the length 755 of the pawl housing 75, permitting the pawl housing 75 to slide longitudinally therein from a first position against the recess proximal end 725 to a second position within the nose assembly recess 748 (dotted line, FIG. 5B).

The nose assembly 74 further has a longitudinal bore 746 that extends from the proximal side 742 to the distal side 744, this bore 746 dimensioned and positioned to permit the inner tube 73 to pass therethrough and slide relatively thereto.

Affixed to the nose assembly's distal side 744 is the proximal end 762 of a generally cylindrical outer tube 76, which has a longitudinal bore 766 that extends from the proximal end 762 to the distal end 764. Tube 76 may be removable affixed to the nose assembly to permit different sizes and configurations of outer tube 76 to be used with delivery device 70. Alternatively, outer tube 76 may include two components (not shown) with the distal section removably attached to the proximal section such that alternative configurations and dimensions of the distal section can be attached to accommodate various anchor configurations and cable diameters. Bore 766 is dimensioned to permit the inner tube 73 to pass therethrough and the anchor proximal portion 310 to slide thereinto. In a preferred embodiment for use with the anchor of FIG. 3, bore 766 is dimensioned to prevent the anchor's distal portion 317 from passing thereinto. This bore 766 is in communication with the nose assembly bore 746. The outer tube 76 preferably has sufficient rigidity to pass through the tissue to be anchored.

The delivery device 70 additionally comprises a pawl 77 that has a longitudinal bore 776 that extends from a proximal side 772 to a distal side 774 and is dimensioned to permit the cable 20 to pass therethrough. The pawl 77 is dimensioned so that its lower portion fits within the pawl cavity 758 and is pivotally attached adjacent a lower proximal corner 759 thereto, at a position lower than the longitudinal bore 756. The pawl 77 is pivotable within the pawl housing cavity 758 between a first position against the pawl housing cavity distal side 761 and a second position against the pawl housing cavity proximal side 763.

The pawl longitudinal bore 776 is positioned in communication with the pawl housing bore 756 when the pawl 77 is in the first position thereby allowing cable 20 to pass freely therethrough. When the pawl 77 is in the second position, however, the bore 776 is positioned sufficiently off-axis to pinch the cable 20 and thereby prevent a longitudinal movement of the cable 20. Thus, placing the pawl 77 in the second position also serves to restrain the cable 20 from longitudinal movement.

The pawl 77 also has a spring bore 777 that extends from the distal side 774 in a proximal direction, but does not extend all the way through to the proximal side 772. A pawl spring 78 is affixed to the nose assembly's proximal side 742 and extends through the pawl housing spring bore 757 and into the pawl spring bore 777 to bear against the pawl 77. This spring 78 thus positioned biases the pawl 77 into the second position, which releasably exerts a longitudinal force on the cable 20 in a proximal direction and by the spring force exerted on pawl 77 biases inner tube 73 to the second position.

The delivery device member 70 elements are relatively dimensioned so that a sliding of the inner tube 73 within the outer tube 76 may be accomplished in a longitudinal direction between two positions. In the first position, the inner tube distal end 734 is in spaced relation to the anchor proximal end 304 when the anchor proximal portion 310 is within the outer tube bore 766. In the second position, the inner tube distal end 734 extends to the outer tube distal end 764, which pushes the anchor proximal portion 310 out of the outer tube 76. As has been seen above this ejection of the anchor proximal portion 310 permits the anchor 30 to flip from its first position to its second position, wherein it can anchor the cable 20 from being pulled in a proximal direction. Spring 78 biases the Pawl housing 75 into the first position.

Figure 6:
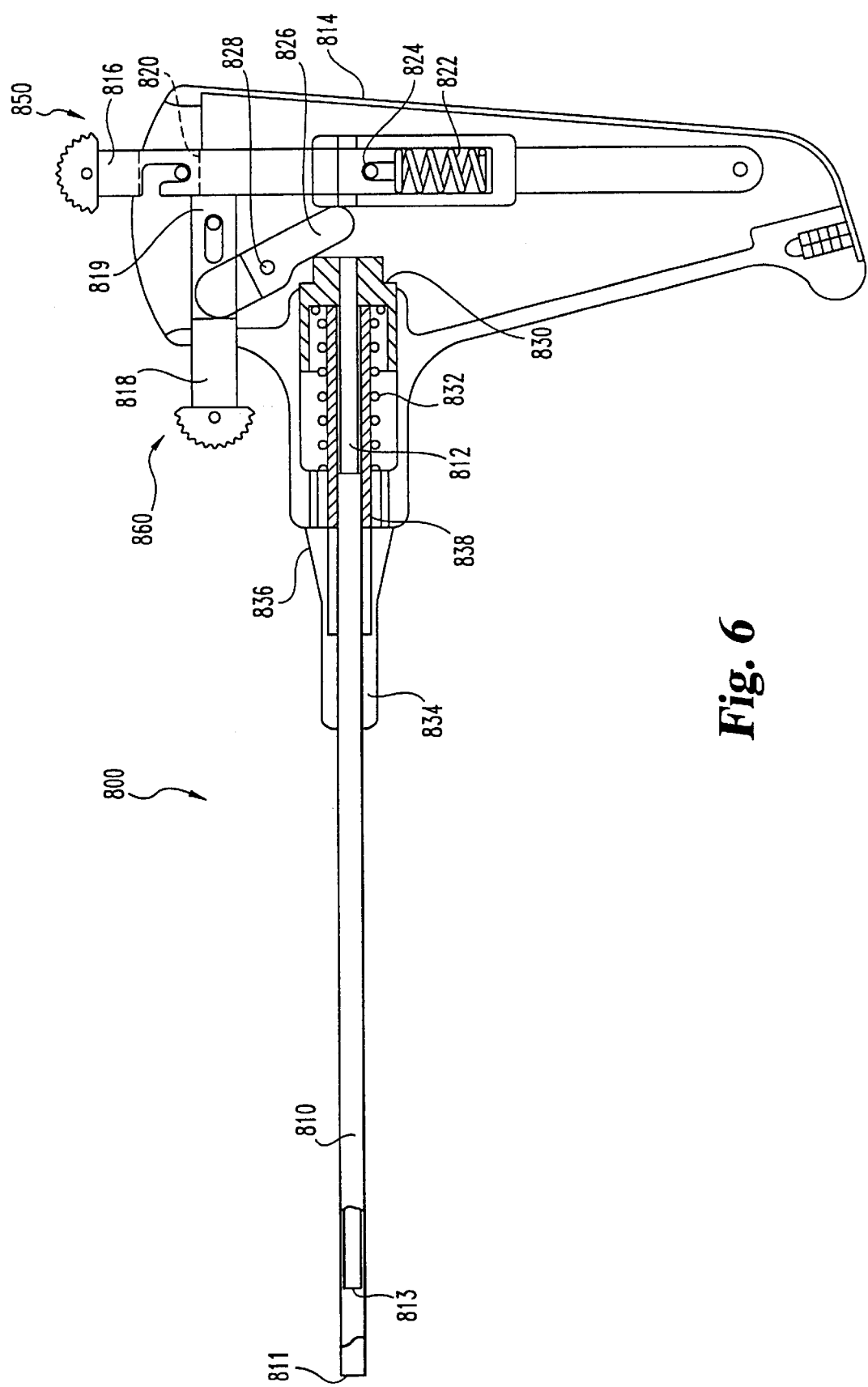
FIG. 6 is a side partial cross-sectional view of still a further embodiment of a delivery device according to the present invention.

Referring now to FIG. 6, a further embodiment of an anchor delivery device according to the present invention is shown. Delivery device 800 has an outer tube 810 including a series of external threads 836 adjacent the distal end that threadedly engage corresponding internal threads 834 to hold outer tube 810 to nose cone 834. Inner tube 812 is slidable within outer tube 810 by a mechanism within housing 814 and controlled between a retracted position with distal end 813 spaced from distal end 811 and an extended position with distal end 813 substantially adjacent distal end 811. Specifically, inner tube 812 abuttingly engages plunger 830 which is biased to a retracted position by spring 832.

Figure 2C:
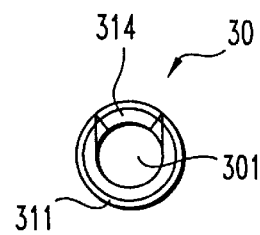
FIG. 2C is a right side view of the anchor of FIG. 2B.
Figure 2B:
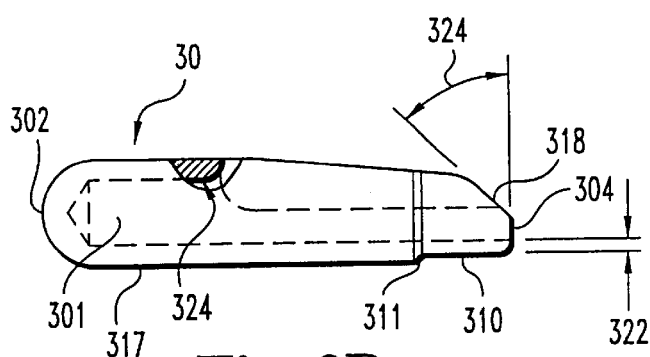
FIG. 2B is a side view of the anchor of FIG. 2A.

As with previously described embodiments, outer tube 810 is sized to receive at least a portion of anchor 30 while inner tube 812 is sized to prevent passage of an anchor such as that shown in FIG. 2. Thus, when tension is applied to a cable (not shown) connected to an anchor (not shown) positioned adjacent distal end 813, the anchor forces inner tube 812 against plunger 830. The cable extends through aperture 824 in plunger 816. As shown in FIG. 6, plunger 816 is biased into a locked position by spring 822. In this position the cable is securely held in aperture 824 to prevent movement. Thus, tension applied to the cable may be maintained in the locked position. Movement of plunger 816 in the direction of arrow 850 into an unlocked position releases the cable.

Movement of plunger 830 is controlled by plunger 818 through lever 826. Movement of plunger 818 in the direction of of arrow 860 moves lever 826 about pivot pin 828 to force the lever against plunger 830 to overcome spring 832 and move plunger 830 against inner tube 812. This movement moves the anchor out of outer tube 810 and permits movement to an anchoring position. In a preferred embodiment, plunger 816 includes a slot (shown in dashed lines) 820 sized to receive a distal portion 819 of plunger 818. In the locked position, shown in FIG. 6, plunger 816 blocks movement of plunger 818 and thus prevents accidental deployment of the anchor. When plunger 816 is moved in the direction of arrow 850, slot 820 is aligned with plunger 818 such that distal end 819 may move into slot 820.

Crimping Tool

The present invention further contemplates a crimping tool for attachment of an anchor to a cable, suture or other elongated member. It being understood that alternative crimping devices may be used to secure anchors to the above described system and that the crimping tool described below may be used or adapted for use with a variety of cabling and suturing systems. The crimping tool of the present system is desirable for the ability to crimp along the axis of a cable at a relatively distant site through a small incision.

Figure 13:
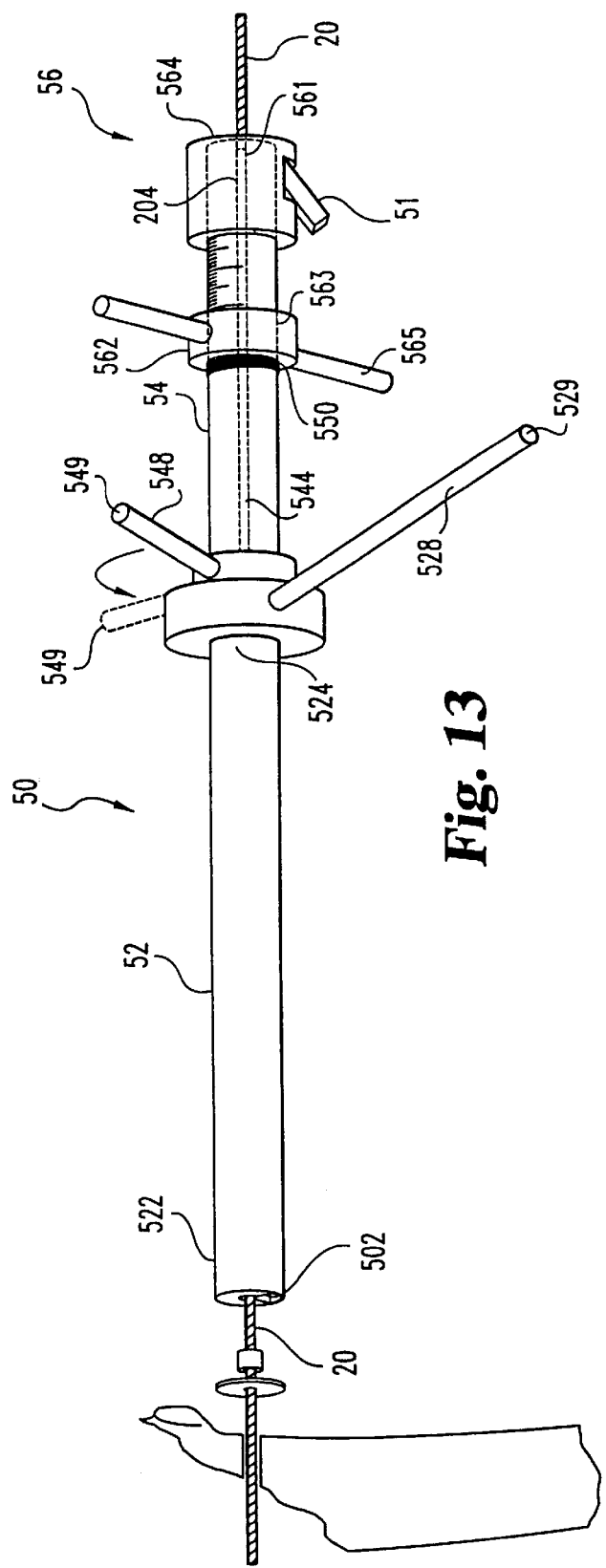
FIG. 13 is a perspective side view of a tensioning, crimping and cutting tool according to the present invention.

Referring now to FIG. 13, crimping tool 50 of the present invention provides several advantages, including a capability of crimping along the longitudinal axis of the cable 20 and of cutting and crimping in one motion. Alternatively, cutting and crimping could be performed separately or by two separate tools with similar function and operation to the single tool shown. The crimping tool 50 comprises an outer elongated generally cylindrical member 52 having a bore 521 from a proximal end 524 to a distal end 522. A first crimping handle 528 is affixed to and extends radially outward from the outer member's proximal end 524.

The crimping tool 50 additionally comprises an inner elongated generally cylindrical member 54 having a bore 541 dimensioned to permit cable 20 to pass therethrough. The inner cylindrical member 54 is dimensioned to fit within the outer cylindrical member's bore 521 and to be rotatable relatively thereto about a common longitudinal axis. A second crimping handle 548 is affixed to and extends radially outward from the inner member's proximal end 544, which extends proximal of the outer member's proximal end 524.

The handles 528 and 548 are rotatable between a first, open position wherein the respective distal ends 529 and 549 are spaced apart by approximately 90 degrees to a second, crimping position wherein the distal ends 529, 549 are generally opposed. Movement of handles 528 and 548 causes inner member 54 and outer member 52 to rotate with respect to each other.

Figure 14A:
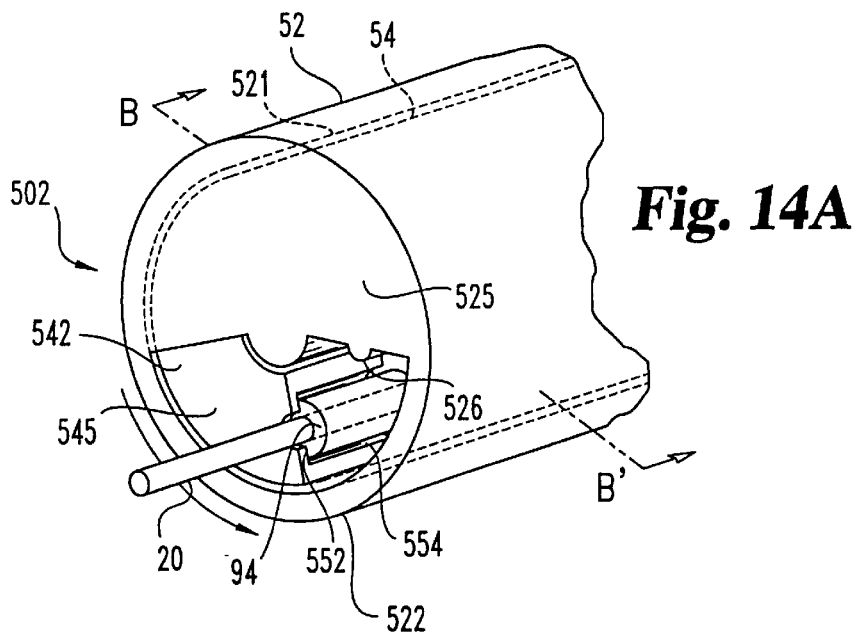
FIG. 14A is a perspective view from the distal end of the tensioning, crimping and cutting tool of FIG. 13.

The crimping means of the crimping tool 50 is illustrated in FIG. 14A, which shows the distal end 502 of the tool 50. The distal end 522 of the outer member 52 has a roughly half-moon-shaped solid portion 525 that obscures approximately half of the bore 541. A protrusion 526 positioned in spaced relation to the longitudinal axis extends radially toward the opening leading to the bore 541.

The distal end 542 of the inner member 54 has a solid portion 545 that obscures the remaining portion of the bore 541 except for a bi-level stepped opening thereinto. Along the distal most portion is a first roughly semicircular cutout 552 dimensioned, together with the outer member's solid portion 525, to closely surround a ferrule 94 therein when the handles 528, 548 are in the open position. The outer member's protrusion 526 is positioned adjacent the cutout 552 when the handles 528, 548 are in the open position.

Longitudinally adjacent to and proximal of the solid portion 545 is a second roughly semicircular cutout 554 dimensioned to permit the cable 20 to freely slide therethrough but too small to permit the ferrule 94 to pass thereinto. When the handles 528, 548 are moved into the crimping position, the first cutout 552 is rotated toward the solid portion 525 and protrusion 526, and a ferrule 94 residing therein is crimped onto the cable 20.

It can be seen that the tool 50 provides the advantage of crimping the ferrule 94 along the longitudinal axis of the cable 20, rather than at a right angle thereto, such as is common in the art, which permits the procedure to be accomplished through a small unitary incision without removing surrounding tissue.

Although a preferred embodiment of the crimping tool of the present invention is shown for use with cable 20 and ferrule 94, it is contemplated that the device may be sized for a specific application. Moreover, it is contemplated that inner member 54 and outer member 52 may have removable distal portions. A variety of sizes and configurations of distal portions may be interchangeable to fit a variety of flexible member and crimp configurations and types. It is contemplated that the cabling, crimp and crimping distal portions may be packaged as a unit to ensure proper use by the end user with a standard crimping tool 50.

Means are also provided for applying longitudinal tension in a proximal direction relative to the tissue to be repaired.

Many devices are know for providing tension to a cable, however, many require a series of pulleys or other change of direction to accomplish the desired tensioning.

In one embodiment (FIG. 13) the inner cylindrical member 54 has an externally threaded proximal portion 550. A generally cylindrical tensioner 56 has a longitudinal bore 561 therethrough from a proximal end 564 to a distal end 562 that is adapted to be mateable with the inner cylindrical member's threaded proximal portion 550. A handle 565 is affixed in radially protruding relation to the tensioner 56 exterior for facilitating a rotation thereof.

The cable-affixing means comprises a cleat 51 positioned adjacent to the tensioner's proximal end 564. The cleat 51, which is analogous to such devices known in the art, is adapted to clamp the cable's proximal end 204 to restrain the cable 20 from moving in a longitudinal direction relative to the inner cylindrical member 54 when in a tightened position. When in a releasing position, the cleat 51 permits the cable 20 to slide there past.

The cable-pulling means comprises the tensioner 56 and the inner cylindrical member proximal end 544, which are relatively movable via a screwing motion therebetween, which serves to change the tension on the cable 20. For example, in use the inner cylindrical member 54 and tensioner 56 are mated, and a cable 20 is inserted through the inner cylindrical member bore 541 and through the tensioner bore 561, and a proximal portion of the cable is clamped by tightening the cleat 51. Unscrewing the tensioner 56 relative to the inner cylindrical member 54 serves to pull the cable 20 in a proximal direction, increasing the tension thereon. The nut could be urged to prevent twisting of cable 20.

Figure 14B:
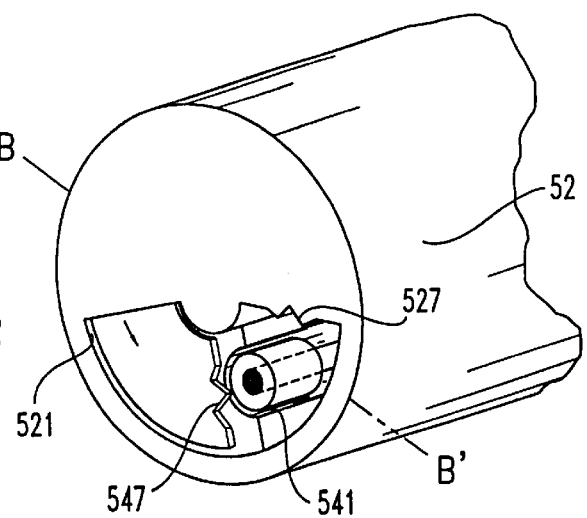
FIG. 14B is a perspective cross-sectional view adjacent the distal end of the tensioning, crimping and cutting tool taken along B–B' of FIG. 14A.

A cutting mechanism is also provided within the tool 50 whereby, when the handles 528, 548 are moved from the open to the crimping position, the cable 20 is cut at a location proximal to or through the ferrule 94. Referring to FIG. 14B, the cutting mechanism comprises two jaws 527, 547, respectively, affixed within the bores 521, 541 of the outer cylindrical member 52 and the inner cylindrical member 54, and are placed into opposition when the arms 528, 548 are closed, cutting the cable 20.

In a particular embodiment the ferrule 94 is typically formed of a metal, such as stainless steel, titanium, or cobalt-chrome alloy. However, in an alternate embodiment the ferrule 94 may be made of a resorbable or non-resorbable polymer material.

Figures 15A, 15B:
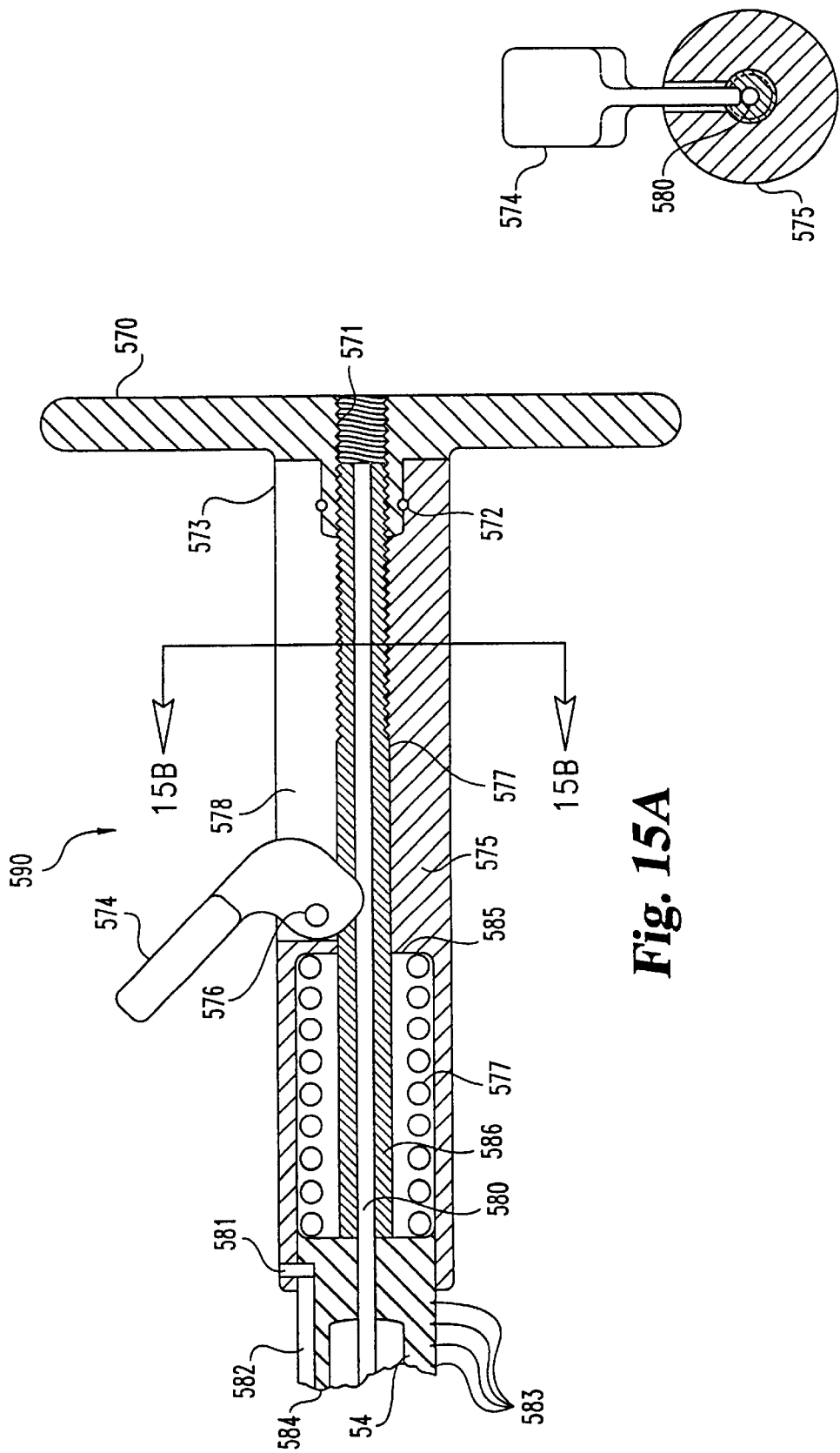
FIG. 15A is a side cross-sectional view of an alternative cable tensioning mechanism for use with the tool of FIG. 13.
FIG. 15B is a cross-section of the mechanism of FIG. 15A taken along line B—B.

The tensioning mechanism shown in FIG. 13 may be replaced with the alternative tensioning mechanism of FIG. 15. The alternative tensioning mechanism 590 attaches to the distal end 584 of the inner member 54. Outer tube 575 is positioned about distal end 584 with spring 577 positioned between the distal end and internal shoulder 585. Inner member 54 includes at least one slot 582 adapted to receive a retaining pin 581 to slidably connect the tensioning mechanism 590. Also disposed on the outer surface of distal end 584 are a series of grooves 583 or other markings to indicate the position of the outer tube 575 with respect to inner member 54. Inner tube 586 includes a cleat 574 pivotally mounted thereon by pivot pin 576. Cleat 574 pivots between a clamping position clamping a cable positioned in channel 580 and a non-clamping position, and extends through slot 578 in the outer tube. Inner tube 586 further includes an externally threaded portion 579. A handle 570 having an internally threaded bore is pivotally mounted on outer tube 575 and is held in place by retaining spring 572. Rotation of handle 571 urges outer tube 575 against spring 577, thereby tensioning a cable (not shown) disposed within channel 580. It will be understood that the tension applied to a cable may be estimated by calibrating the spring force applied as outer tube 575 is adjacent each index marking 583.

Figure 16:
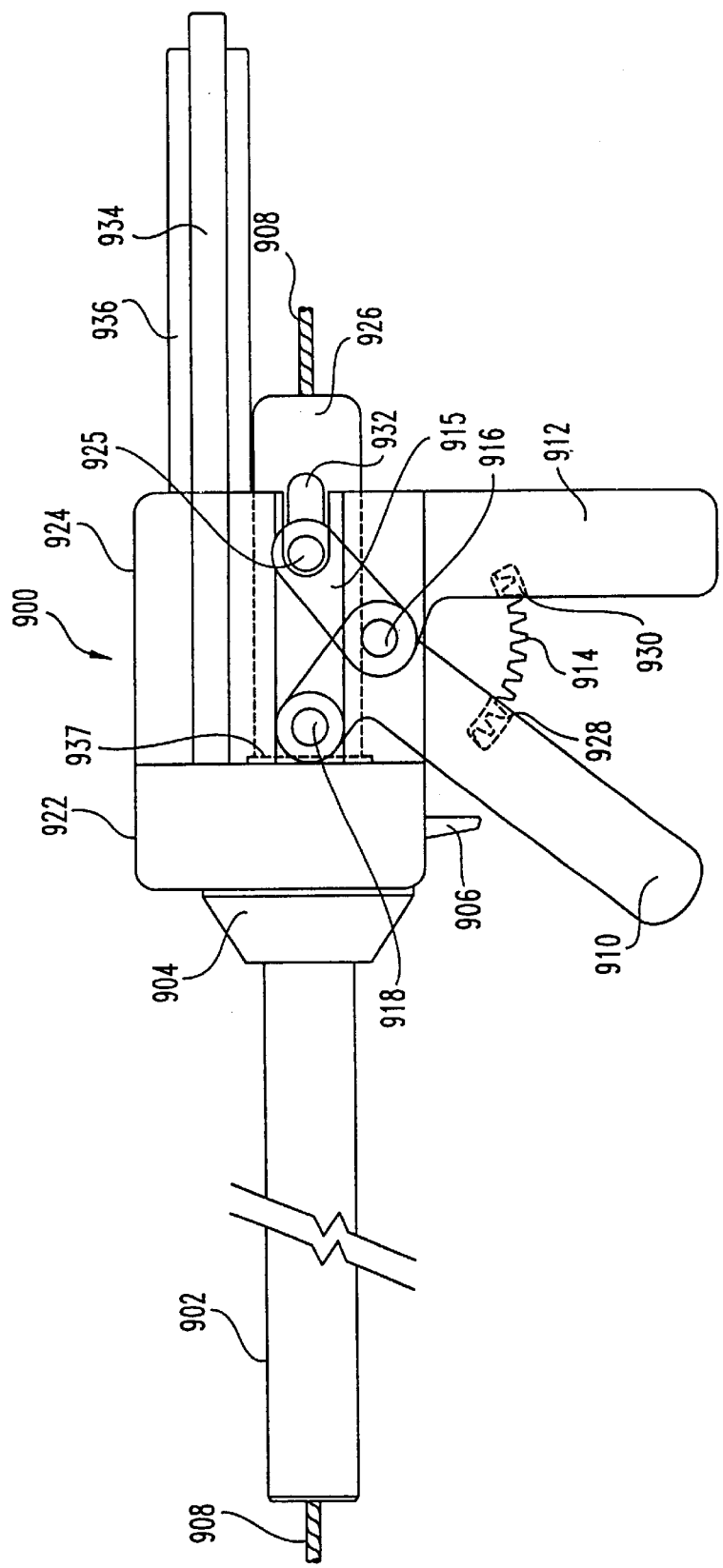
FIG. 16 is a side view of an alternative embodiment of a tensioning, crimping and cutting tool according to the present invention.

A further embodiment of a tensioning, crimping and cutting tool according to the present invention is disclosed in FIG. 15. The crimping tool 900 includes an outer tube 902 attached to a nose 904. This nose is attached to a front housing 922 which is interconnected with rear housing 924. As shown in the partial cross-section view of FIG. 16, inner tube 901 is disposed within outer tube 902 and includes a bore 917 for receiving cable 908. The position of cable 908 within inner tube 901 is maintained with respect to movement toward the distal end 905 by trigger pawl 906. Trigger pawl 906 is pivotally connected to front housing 922 by pivot pin 939. As shown in FIG. 16, spring 938 biases trigger pawl 906 into the cable retaining position with engaging end 907 engaging cable 908 adjacent the proximal end of inner tube 901. Trigger pawl 906 may be moved to a disengaged position by overcoming the force of spring 938 and moving trigger pawl 906 within slot 940 such that engaging end 907 disengages cable 908.

Rear housing 924 includes a cable tensioner assembly 926 for applying tension to cable 908 towards the proximal end 913. Tensioning assembly 926 is operable between a tensioning position and the released position shown in FIG. 16, by movement of handle 910 with respect to handle 912. Handle 910 is pivotally attached to rear housing 924 by pivot pin 918. A linking bar 915 is joined to handle 910 by pivot pin 916 and interconnects the handle with tensioning assembly 926 through pivot pin 924. Movement of handle 910 towards handle 912, fixedly connected to rear housing 924, causes tensioning assembly 926 to move proximally.

Referring now to FIG. 16, tensioning assembly 926 includes a pair of pawls that grip cable 908 when tensioning assembly 926 is displaced proximally and that allow passage of the cable when tensioning assembly is moving distally. Pawl 941 is pivotally connected to the tensioning assembly 926 by pivot pin 942. The pawl is urged into a locking position by spring 943. The pawl opposing pawl 941 is identical. Tensioning assembly 926 further includes a set of belleville springs 944 that may be adjusted by movement of threaded shaft 945 to increase or decrease the pressure applied to the cable when the gripping teeth of the pawls are disengaged with the wire as the tensioning assembly is drawn forward. Springs 944 maintain the position of pin 924 within slot 932. Spring 914 disposed between handles 910 and 912 in openings 928 and 930 respectively, urges handle 910 forward. This movement also urges tensioning assembly pawls against front wall 937 which in turn urges the pawls into a disengaged position shown in FIG. 16.

In operation, tensioning assembly 926 is moved to apply proximal tension to cable 908. As previously described, trigger pawl 906 permits proximal movement of the cable. Once proximal tension is released by the tensioning assembly, trigger pawl 906 engages cable 908 to prevent distal movement and thereby maintain the tension while the pawls of the tensioning assembly are disengaged to permit the assembly to return to a forward position. This process may be continued until the desired amount of cable tension has been achieved.

Figure 17:
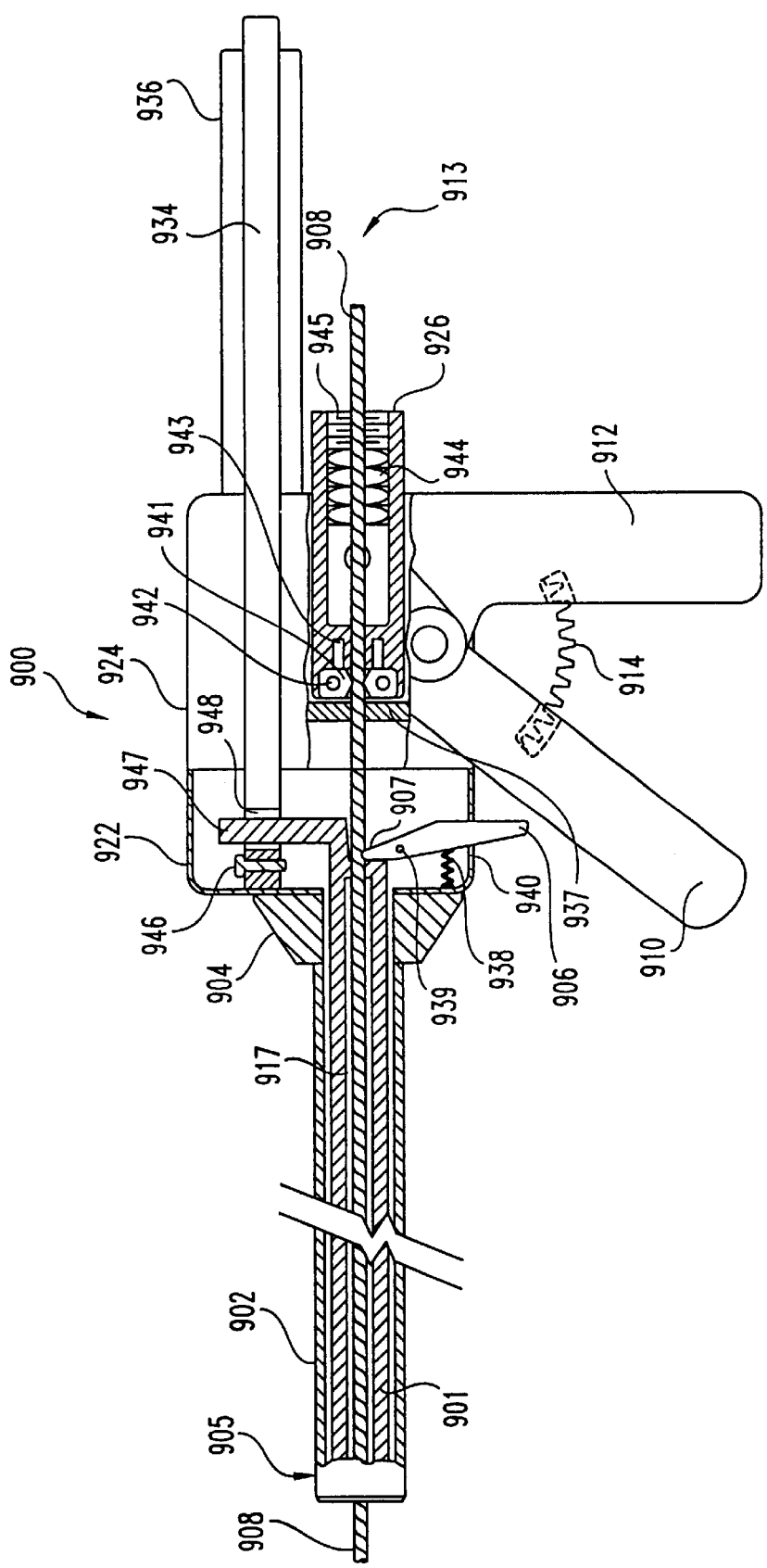
FIG. 17 is a partial cross-sectional view of the tool of FIG. 15.

Cable tensioner, crimper and cutter 900 also includes crimping and cutting handles 934 and 936. Referring to FIG. 17, handle 936 is fixedly attached to rear housing 924 while handle 924 is connected by pivot pin 946 to front housing 922. The handles are biased into a separated position by spring 949 mounted on projection 950 of handle 934 and received within opening 951 in the rear housing. Handle 934 includes a slot 948 for receiving an inner tube extension 947 (FIG. 16). Linear movement of handle 934 toward handle 936 is translated into rotation of inner tube 901 by the engagement of inner tube extension 947 in slot 948. The distal end 905 of inner and outer tubes 901 and 902 are configured as shown in FIGS. 14A and 14B such that rotation of the inner tube in relation to the outer tube results in crimping a ferrule and cutting a cable.

Figure 18:
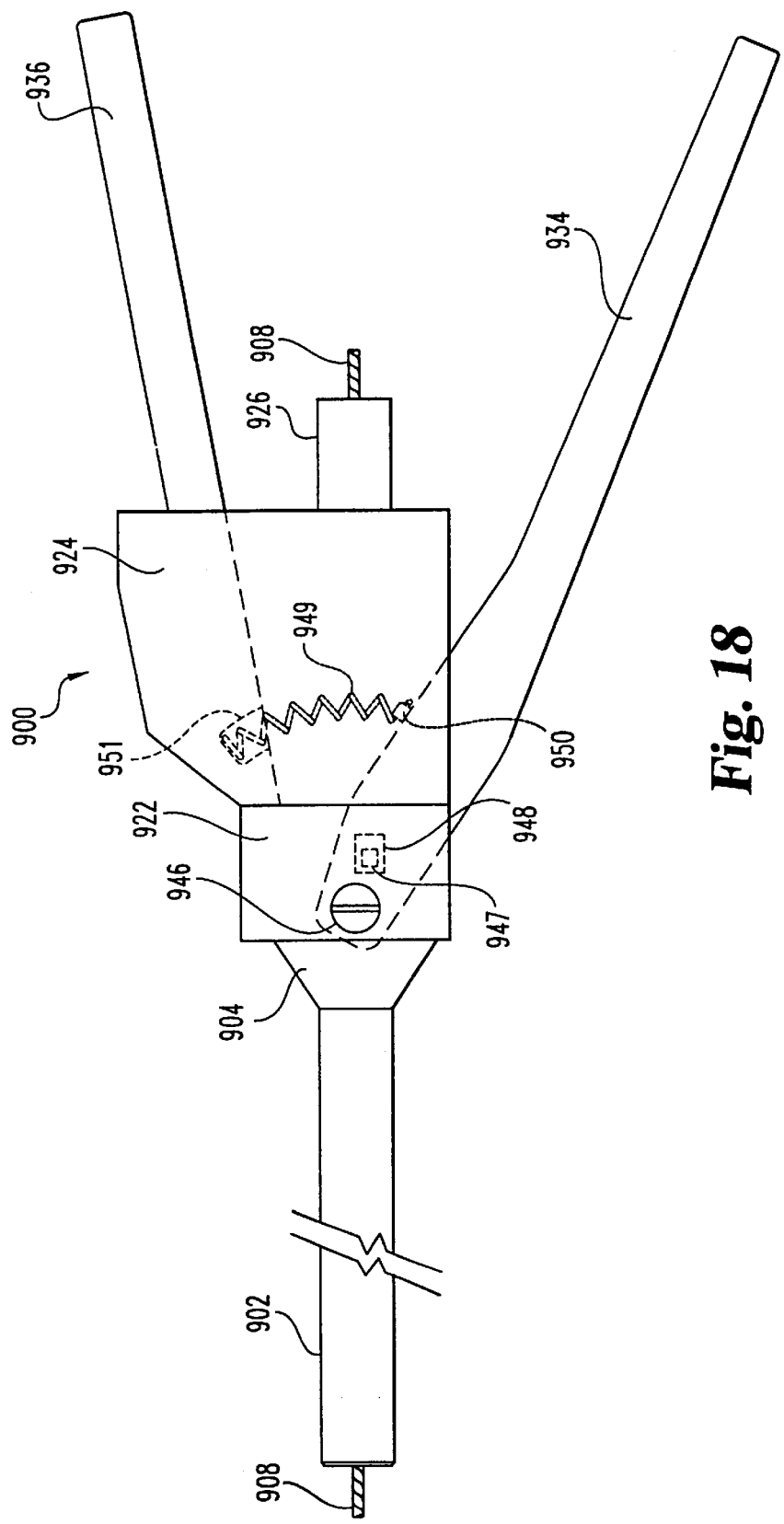
FIG. 18 is a top view of the tool of FIG. 15.
Figure 19:
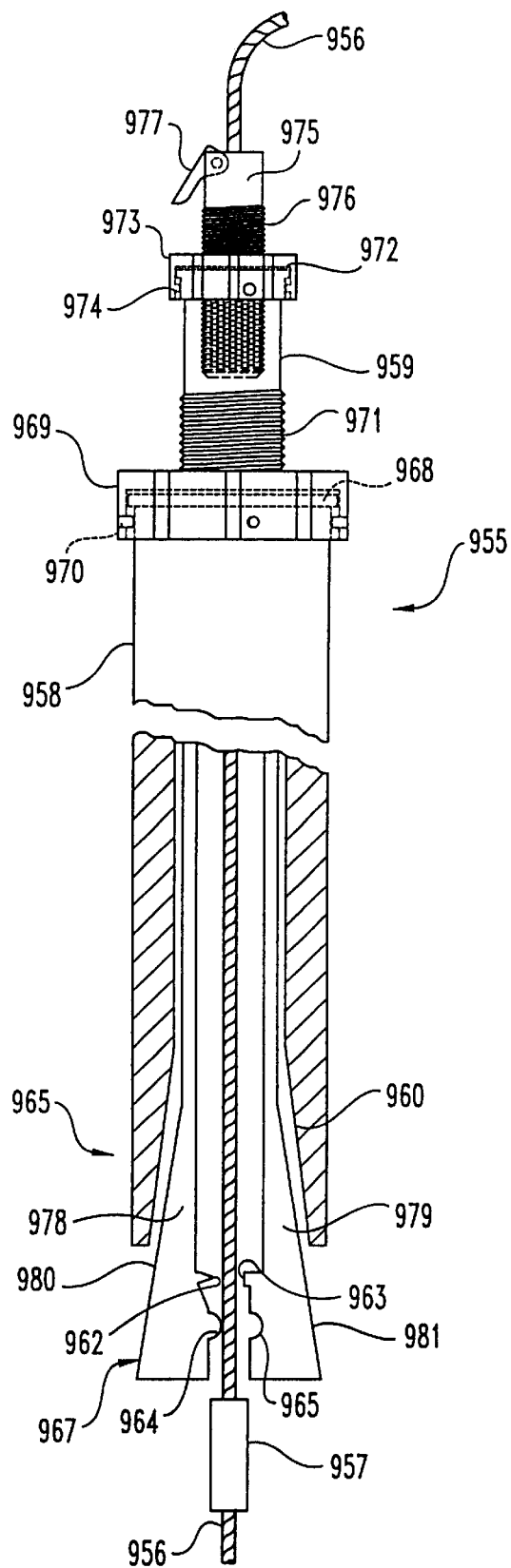
FIG. 19 is a front partial cross-sectional view of still a further embodiment of a tensioning, crimping and cutting tool according to the present invention.

Still a further embodiment of a tensioning, crimping and cutting tool according to the present invention relies on longitudinal movement of the components rather than rotational movement. Referring to FIG. 18, a tensioning, crimping and cutting tool 955 includes an inner member 959, an outer member 958 and a cable retaining assembly 975. Cable retaining assembly 975 is preferably received within inner member 959 and includes a cleat 977 pivotally mounted to be moveable between a disengaged position and an engaged position securely holding cable 956. Retaining assembly 975 further includes a threaded section 976. Inner member 959 includes a flange 972. An internally threaded nut 973 is disposed about flange 972 and engages threaded section 976. Nut 973 is rotatably maintained in position by mounting pins 974.

Inner member 959 includes an externally threaded section 971 adjacent flange 972 and at an opposite end, a pair of spaced branches 978 and 979, each having a flared section 980 and 981, respectively. Branch 978 includes a cutting blade 962 and a crimping projection 964 while branch 979 includes a corresponding cutting anvil 963 and crimping depression 965. It is contemplated that inner member 959 may include more than two branches and may have multiple projections disposed adjacent distal end 967.

Inner member 959 is disposed within a preferably tubular outer member 958. Outer member 958 includes an inclined surface 960 adjacent distal end 966. Opposite the inclined surfaces is a flange 968. Nut 969 is disposed about flange 968 and pivotally retained there by mounting pins 970.

In operation, cable 956, having a distal end anchored in a tissue section (not shown), is threaded through inner member 959 and cable retaining assembly 975. A ferrule 957, slidable along cable 956, is positioned within branches 978 and 979 adjacent crimping projection 964 and crimping depression 965. Cleat 977 is rotated to engage cable 956. Nut 973 is rotated about external threads 976 to move the cable retaining assembly with respect to the inner member, which bears against a section of tissue (not shown), and thereby applies tension to cable 956. Once the desired amount of tension is applied, nut 969 is rotated with respect to threads 971 to urge outer member 958 downward toward ferrule 957. As outer member 958 advances, branches 978 and 979 are urged toward each other by acting against inclined surface 960. Thus, cutting blade 962 and cutting anvil 963 cooperate to cut cable 956 while crimping projection 964 and crimping depression 965 crimp ferrule 957 to securely engage cable 956.

While threaded engagements have been illustrated for applying cable tension and for moving the outer member, it is contemplated that other mechanisms known to those skilled in the art may be applied to the device described herein. Moreover, nut 973 may be engaged by a torque wrench to provide the user with an estimate of the tension applied to cable 956.

Variations of the present longitudinal crimping tool are within the spirit of the present invention, such tools utilizing movement preferably occurring within the outer tube such that the opening in the tissue is not significantly enlarged beyond the diameter of the outer tube as a result of the crimping process.

Alternative Anchor Embodiments

Figure 9:
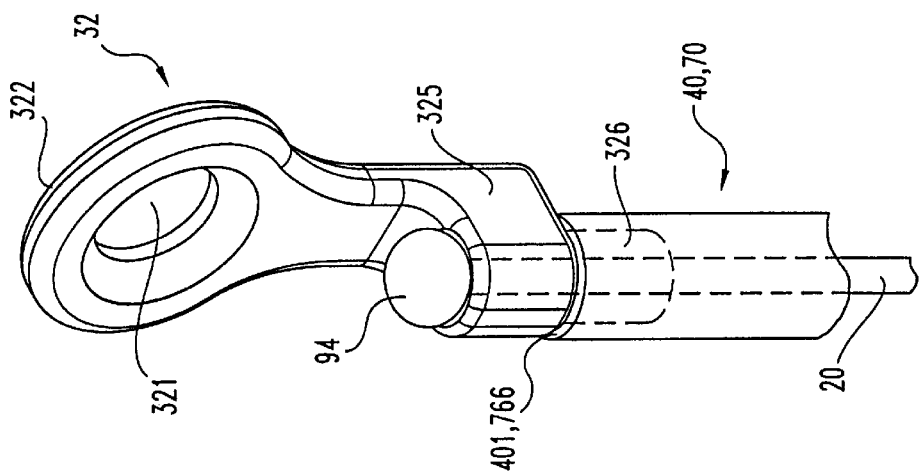
FIG. 9 is a front perspective view of an eyelet anchor according to the present invention mounted on a delivery device.
Figure 10:
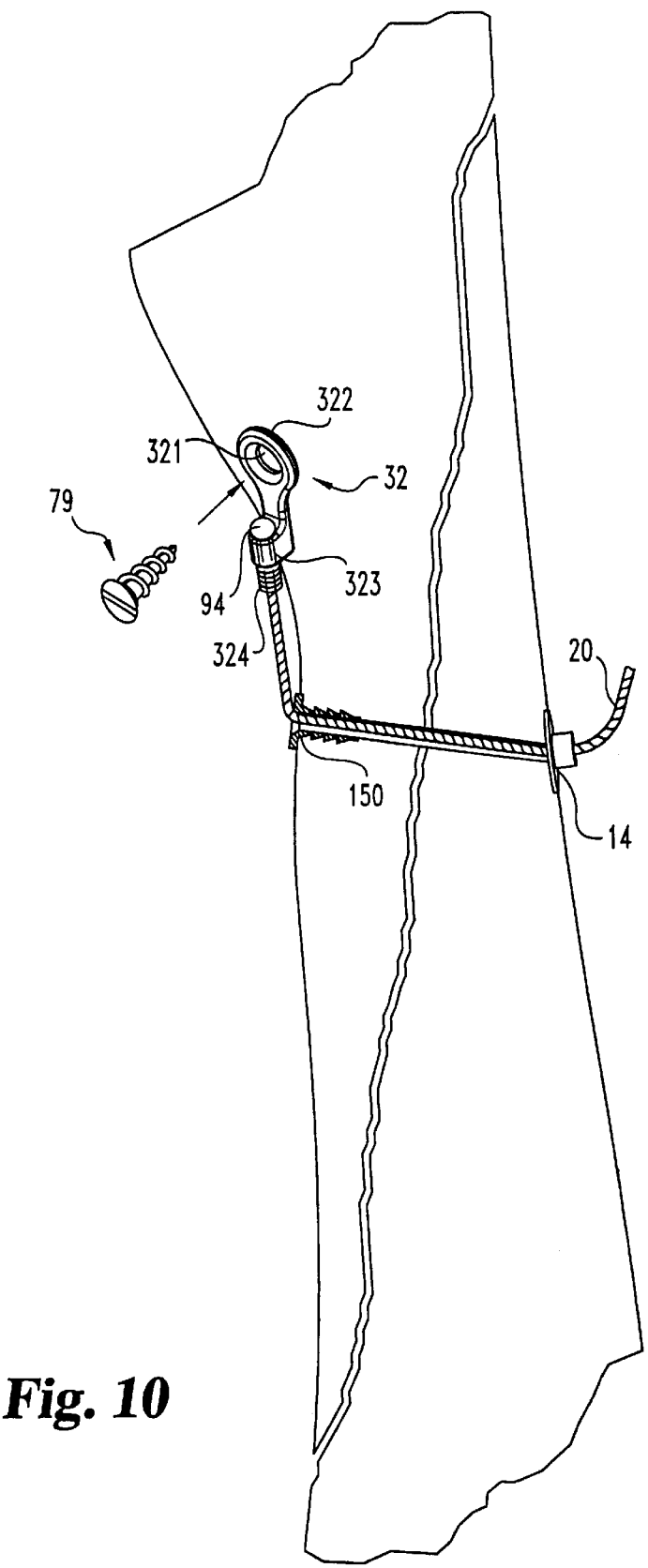
FIG. 10 is a front perspective view of the eyelet anchor of FIG. 9 being affixed to a bone with an attached cable extending through a bone opening protector and secured by a second anchor.

An alternate form of a tissue anchor comprises an eyelet anchor 32, the structure and function of which are illustrated in FIGS. 9 and 10. The eyelet anchor 32 is affixed at a proximal end 324 to the cable distal end 202, and the eyelet anchor 32 has an eyelet hole 321 at a distal end 322 for receiving an anchoring screw 79. The eyelet anchor 32 also has a cable bore 323 adjacent the proximal end 324 adapted to permit cable 20 to pass therethrough and to be crimped therein.

Figure 4:
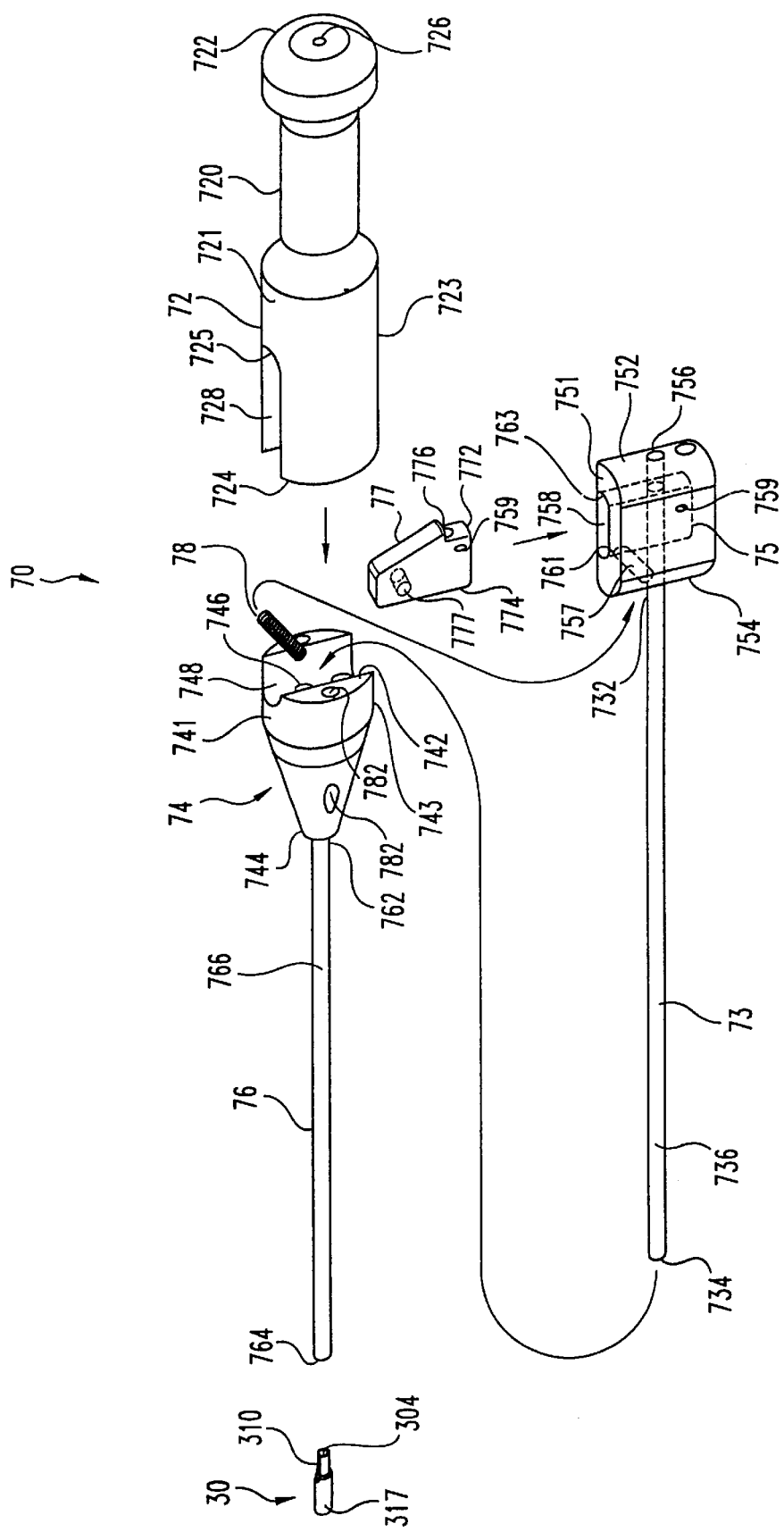
FIG. 4 is an exploded perspective view of an alternate embodiment of a delivery device according to the present invention.

The delivery devices of FIGS. 1, 4 or 6 are also usable with the eyelet anchor 32 described above. In this case, the eyelet anchor 32 has a central portion 325 that is dimensioned larger than the distal portion of the delivery device member cylindrical portion bore 401 or 766. The eyelet anchor 32 further has a proximal portion 326 that is dimensioned to reside within the distal portion of the delivery device member cylindrical portion bore 401 or 766. Thus, as above, the eyelet anchor proximal portion 326 is retainable within the bore 401 or 766 when the cable 20 to which it is attached is under longitudinal tension in a proximal direction. Alternatively, it is contemplated that eyelet anchor 32 is formed of a deformable material which tends to resume its original shape. It will be understood that an eyelet anchor 32 formed of such a material may be deformed to be received within outer tube 76, such that inner tube 73 will force eyelet anchor 32 out of outer tube 76. The anchor may then resume its larger original dimensions.

Figure 11A:
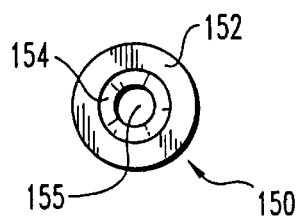
FIG. 11A is a front view of a bone opening protector according to the present invention.
Figure 11B:
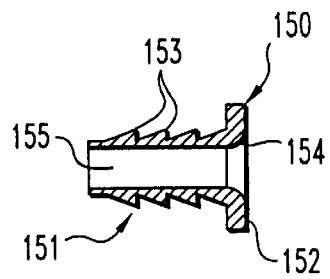
FIG. 11B is a side cross-sectional view of the bone opening protector of FIG. 11A.

The present invention also contemplates the use of a bone opening protector 150 as shown in FIGS. 10 and 11. Opening protector includes a surface engaging portion 152 adapted to engage the exterior surface of the bone adjacent the opening to prevent advancement into the bone. Opening protector 150 also includes a cylindrical portion 151 that extends into the bone opening and provides a lumen for passage of cable 20. Preferably, the exterior surface of the cylindrical portion 151 includes a roughened surface to engage the surrounding bone to prevent dislodgement. While it is contemplated that the roughened surface may be threads such that the protector may be screwed into the opening, preferably, the surface includes a series of circular projections 153 having an inclined leading edge for ease of insertion and a cavity adjacent the trailing edge to inhibit removal. Also, it is contemplated that cylindrical portion 151 could be substantially eliminated and anchoring elements could extend through, or be a part of, surface engaging portion 152.

It is intended that the surface engaging position 152 lie substantially flush with the surface of the bone. Thus, for openings created perpendicular to the surface of the bone, cylindrical portion 151 and surface engaging portion 152 will be perpendicular. In a preferred embodiment, the corner 154 between the cylindrical portion 151 and surface engagement portion 152 is rounded. This is intended to limit the abrasion and wear on the anchoring member as it slides across the corner. The protector is particularly useful in applications were the cable or suture will be pulled against the corner of the bone opening. As shown in FIG. 10, eyelet anchor 32 secured by bone screw 79 and cable 20 extends through opening protector 150. Tension is applied to cable 20 and is maintained by crimped ferrule 94 bearing against washer 14. Without opening protector 150, cable 20 would have a tendency to cut through the edge of the bone opening causing damage to surrounding tissue and reducing the tension on cable 20.

Tissue Anchoring Method

Figure 8:
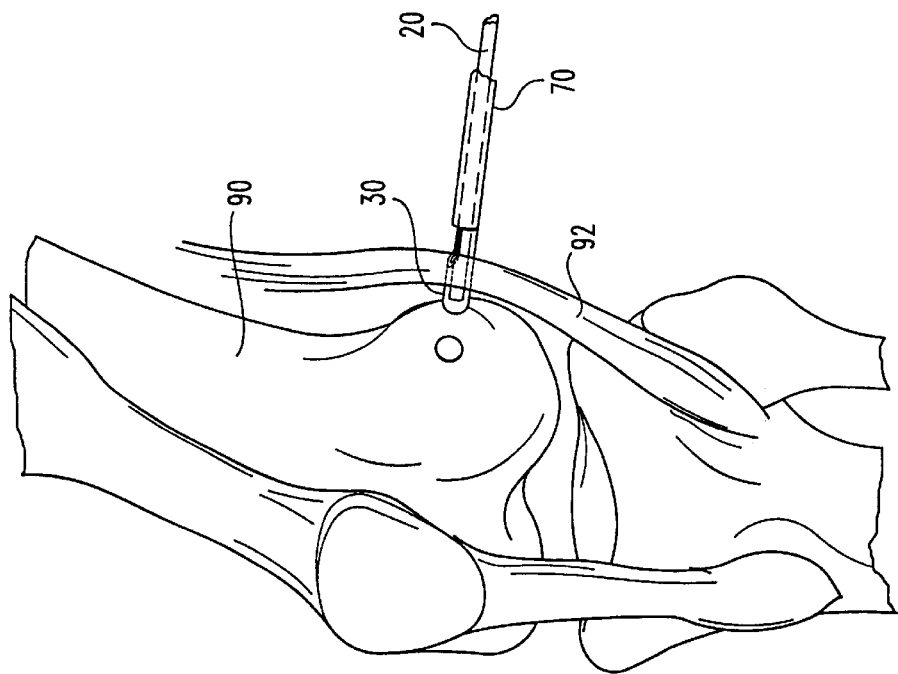
FIG. 8 illustrates the insertion step of the method of use of the system in anchoring a ligament to a bone.

The method for utilizing the above-described system comprises the following steps, as shown in FIGS. 12A–E, for anchoring two sections of bone together. It is obvious to one skilled in the art that the same technique is applicable to a method for anchoring two different bones together, for anchoring other types of tissue together, or for anchoring another type of tissue to bone [see, e.g., FIG. 8, illustrating the anchoring of a ligament 92 (here, a medial collateral ligament) to a bone 90 (here, the tibia)]. Therefore, no limitations are intended by the presentation of this exemplary embodiment.

Two holes 115 and 116 are drilled through the bone sections 90 and 91, the cable/anchor/delivery device 20/30/40 combination is inserted through the holes 115, 116 until the anchor 30 is completely through the distal hole 115 (FIG. 12A). Although drilled holes are illustrated, it is contemplated that anchor 30 may include a sharp tip such that the anchor may be pushed through unprepared bone or other tissue. The cable tension is released, which permits the anchor 30 to rotate and be restrained on the distal side of the distal hole 115 (FIG. 12B). In addition to the anchor disclosed herein, it is contemplated that the insertion device could also be used with an anchor designed to be embedded within the bone, i.e. the anchor would not exit the distal cortical bone and instead would be deployed in the cancellous bone.

Figure 12D:
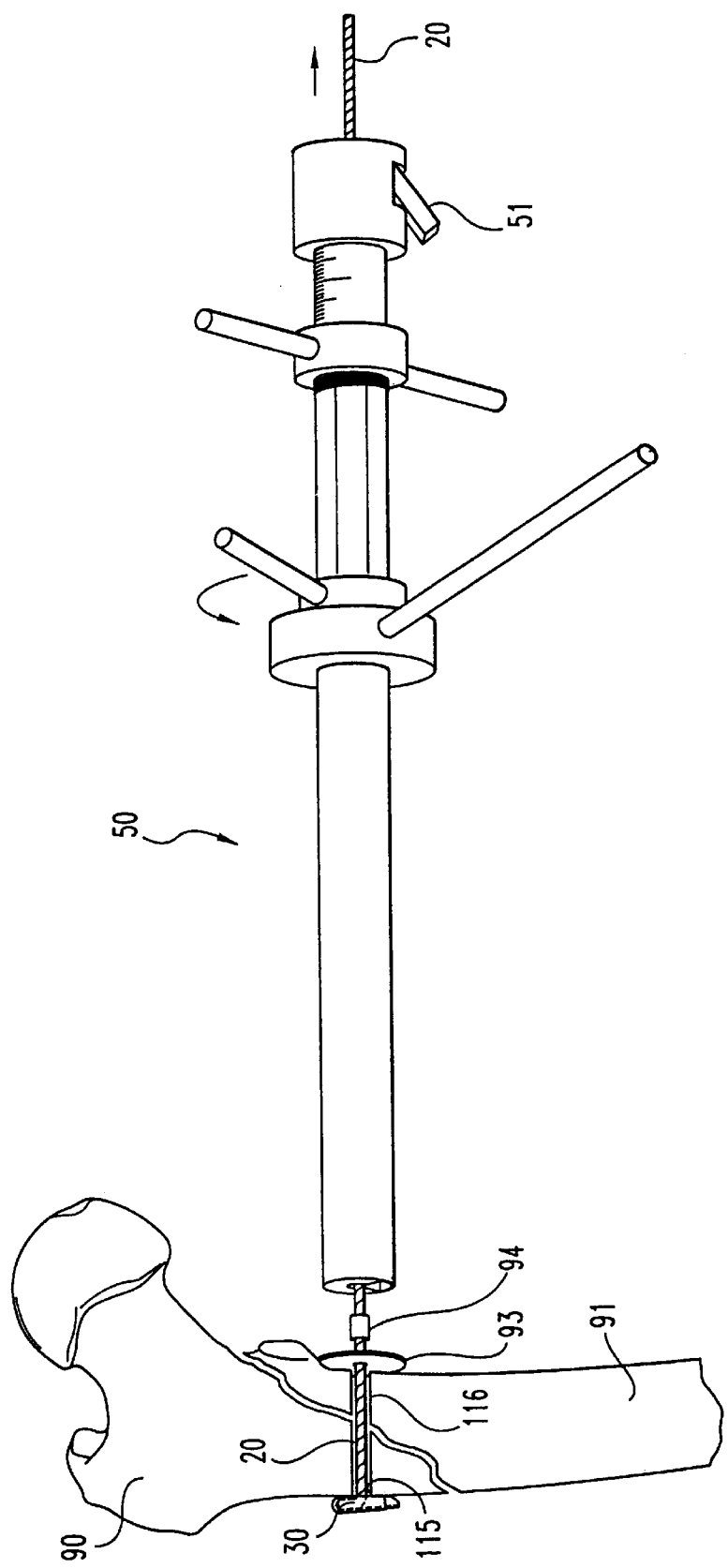
FIGS. 12 (A–E) illustrates a method of use of a system according to the present invention in anchoring two sections of bone together.
In FIG. 12A the delivery system with anchor and attached cable are inserted through the bone.
In FIG. 12B the anchor is pivoted.
In FIG. 12C a washer and a ferrule are threaded onto the proximal end of the cable, and in FIG. 12D the ferrule is crimped onto the cable, and the cable is cut, leaving the bone fragments anchored as shown in FIG. 12E.

The delivery device 30 is removed from the cable 20, and a washer 93 and ferrule 94 are threaded onto the cable to a position adjacent the proximal hole 912 (FIG. 12C). The cable 20 is then inserted into the crimping tool 50 sufficiently far that the ferrule 94 is positioned within the first cutout 552 adjacent the second cutout 554. The cable 20 is clamped with the cleat 51 and pulled to a desired tension (FIG. 12D). Tensioner 56 may be unscrewed with respect to inner cylindrical member 54 while cleat 51 securely holds cable 20, thereby pulling the bone fragments together and applying measurable compression between the fragments. The crimping tool 50 is closed to crimp the ferrule 94 onto the cable 20 and also to cut the cable 20 (FIG. 12E). Alternatively, the crimp may be made first, and then a separate cable cutting tool (not shown) can be used for thicker types of cable.

If desired, an eyelet anchor 60, such as shown in FIG. 9, may also be used. In this case, the eyelet anchor 60 is threaded onto the cable 20 via cable bore 602, which is at the proximal end 601, before the ferrule 94 is threaded on, and, after the crimp is made, a screw 61 is inserted through the screw hole 604, which forms the eyelet, and into the bone 90 to attach the eyelet anchor 60 (FIG. 9).

The method described above may be performed utilizing any combination of the delivery devices and tensioning, crimping and cutting tools described herein.

Suture Material Anchoring System and Method

Figure 7B:
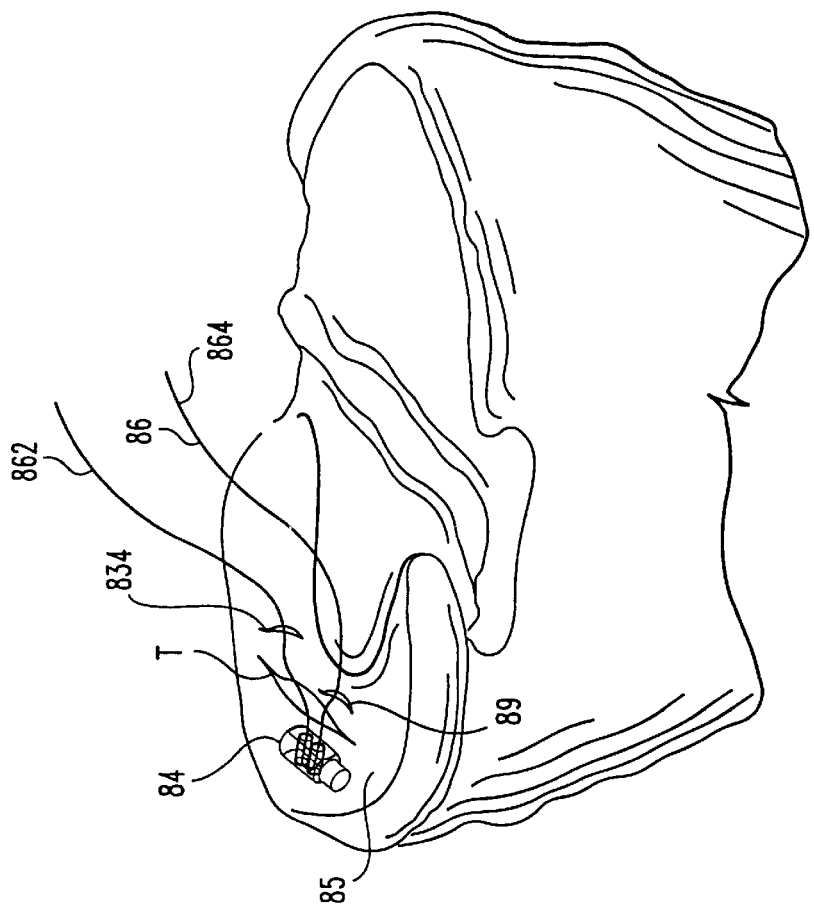
FIG. 7B illustrates the suture anchor of FIG. 7A being used in repairing a soft tissue tear.
Figure 7A:
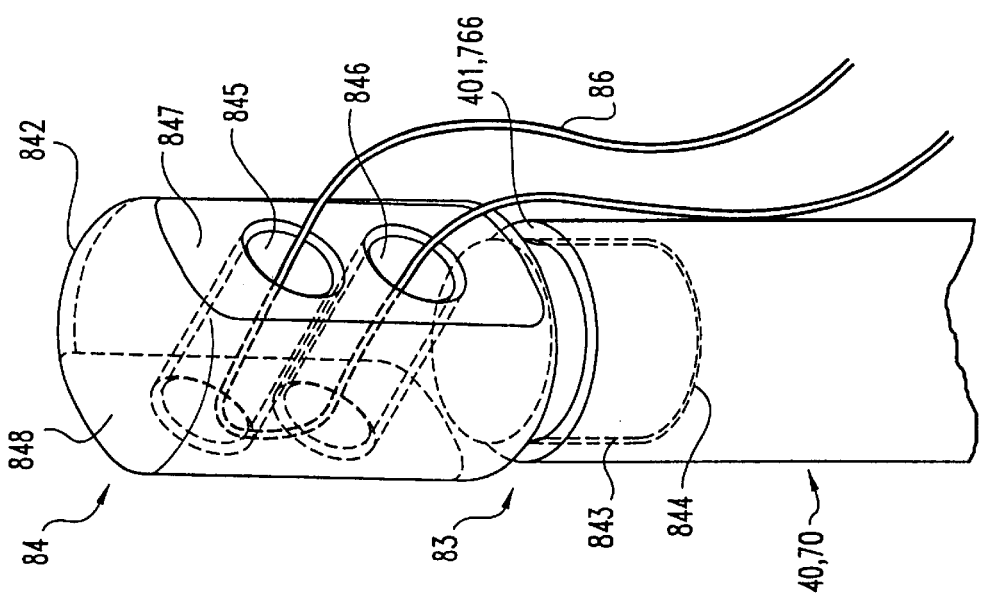
FIG. 7A illustrates a suture anchor according to the present invention supported by a delivery device's distal end.

A suture material anchor system 83, as shown in FIG. 7A for repairing soft tissue, comprises a suture anchor 84 for use with a delivery device, such as either of the delivery devices 40, 70 or 800 as described above.

The suture anchor 84 is an elongated member having a longitudinal axis extending from a proximal end 844 to a distal end 842. The suture anchor 84 also has a pair 845, 846 of cross-bores extending from a first side 847 through to a second, opposed side 848. Cross-bores 845, 846 are dimensioned to permit suture material 86 to pass therethrough. In use suture material 86 is threaded through bore 845 from the first side 847 to the second side 848 and then through the other bore 846 from the second side 848 to the first side 847.

The suture anchor 84 has a narrowed proximal portion 843 at the proximal end 844, proximal of the cross-bores 845, 846, that is dimensioned to be insertable into and supported by the impeller bore 401 or the outer tube bore 766, as previously described for the pivotable anchor 30. The central portion 848 is dimensioned too large to be insertable into the impeller bore 401 or the outer tube bore 766. The suture anchor 84 has a first cross-sectional dimension generally along the longitudinal axis greater than a second cross-sectional dimension generally perpendicular to the longitudinal axis, as before for the pivotable anchor 30.

The suture anchor 84 is manipulable and pivotable by pulling the ends of the suture material, which can accomplish a bracing of the suture anchor 84 against the distal side of the tissue 85 to be repaired. In use, the ends of the suture material 86 are retainable outside the incision, or, alternatively, one end 862 can be retained outside the introducing incision 88, and a second end 864 can be pulled through a second incision 89, as shown in FIG. 7B.

A method of using the system 83 to repair a soft tissue tear such as a meniscal tear T comprises the steps of piercing the tissue 85 across the tear T, inserting the delivery device/suture material/anchor system into the pierced hole 834, manipulating the delivery device so that the anchor 84 emerges from the far end of the tear T and rotates so that the anchor 84 has its length generally perpendicular to the tear T and thus will not slip out. The surgeon can then manipulate the suture material 86 and tie it off as desired to secure the repair. Alternatively, a second incision 835 may be made at an adjacent site across the tear T, as shown in FIG. 7B, and the two pieces of suture material then joined together to strengthen the repair. The anchor 84 can either be inserted into the body of the tissue 84, as shown in FIG. 7B, or it can be impelled completely through the tissue (not shown), depending upon the application, to anchor the suture material 86.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A method for attaching a first section of tissue to a second section of tissue, the method comprising the steps of:

providing an anchor member having a first dimension larger than a second dimension, the anchor member affixed to a first end of a cable;

inserting the anchor member in combination with the cable into a bore of a delivery device, the bore having a longitudinal axis, a distal end of the anchor member retained outside the delivery device bore, a proximal end of the anchor member inserted into and supported by the bore of the delivery device;

maintaining tension on the cable within the delivery device to retain the anchor member proximal end within the delivery device bore and to maintain the first dimension in alignment with the longitudinal axis;

impelling the anchor member in combination with the insertion device through the first tissue section and then through the second tissue section;

releasing the tension on the cable;

pivoting the anchor member to a position wherein the anchor member first dimension is generally transverse to the bore longitudinal axis;

applying tension to a second end of the cable to force the anchor against a distal side of the second tissue section and to urge the first tissue section into close opposition with the second tissue section;

affixing a retainer to the cable adjacent a proximal side of the first tissue section; and cutting the cable proximal the retainer.

2. The method of claim 1, wherein the first section of tissue and the second section of tissue includes cortical bone.

3. The method of claim 2, wherein the anchor member is a rigid material sufficient to withstand the force applied to compress a fracture between the first cortical bone section and the second cortical bone section.

4. The method of claim 3, wherein the anchor member is stainless steel.

5. The method of claim 3, wherein the cable has sufficient tensile strength to withstand the force applied to compress a fracture between the first bone segment and the second bone segment.

6. The method of claim 5, wherein the cable is medical grade steel.

7. The method of claim 1, wherein said affixing is performed by deforming a portion of the retainer to engage the cable.

8. The method of claim 7, wherein the method is performed through a unitary incision in the human body.

9. The method of claim 7, further including:

providing a crimping and tensioning tool having an outer member and inner member movably disposed within the outer member;

sliding a retainer on the cable after said pivoting step;

inserting the cable into the crimping and tension tool outer member;

performing said applying tension step utilizing the crimping and tensioning tool to urge the retainer toward the anchor member; and moving the inner member with respect to the outer member thereby deforming a portion of the retainer.

10. A method for joining two segments of tissue, comprising:

providing a first anchor, an elongated member attached to the first anchor, a second anchor slidable on the elongated member and having a deformable portion adapted to engage the elongated member, and a crimping tool having an outer member and an inner member movably disposed within the outer member;

inserting the elongated member through a proximal tissue segment and a distal tissue segment;

anchoring the first anchor to the distal tissue segment;

sliding the second anchor on the elongated member adjacent the proximal tissue segment;

threading the elongated member through the crimping device;

applying tension on the elongated member to urge the distal tissue segment toward the proximal tissue segment; and moving the inner member with respect to the outer member thereby deforming the deformable portion of the second anchor and maintaining the tension applied to the elongated member.

11. The method of claim 10, wherein the two segments of tissue include cortical bone.

12. The method of claim 11, wherein the anchor is at least as rigid as cortical bone and the elongated member is more flexible than cortical bone.

13. The method of claim 12, wherein the anchor is pivotable relative to the elongated member between a first position wherein a longitudinal axis of the first anchor is in substantial alignment with a longitudinal axis of the elongated member, and a second position wherein the longitudinal axis of the first anchor is substantially transverse to the longitudinal axis of the elongated member; said inserting including inserting the first anchor through the proximal and distal tissue segments in the first position and said anchoring includes pivoting the first anchor into the second position.

14. The method of claim 13, further including positioning a washer on the elongated member prior to said sliding.

15. The method of claim 11, further including positioning a bone opening protector adjacent to the proximal tissue segment prior to said sliding to inhibit the elongated member or second anchor from cutting into the bone.

16. The method of claim 10, wherein said moving is rotating said inner member with respect to said outer member.

17. The method of claim 10, wherein the crimping tool includes a tensioning apparatus and a cutting apparatus, and said applying tension includes operating the tension apparatus to exert tension on the elongated member and further including operating the cutting apparatus to cut the elongated member adjacent the second anchor.

18. A method for joining two cortical bone segments, comprising:

providing a first rigid anchor pivotally connected to an elongated flexible member, the first rigid anchor moveable between an insertion position wherein a longitudinal axis of the first anchor is in substantial alignment with a longitudinal axis of the elongated flexible member, and an anchor position wherein the longitudinal axis of the first rigid anchor is substantially transverse to the longitudinal axis of the elongated member, a second deformable anchor slidable along the elongated flexible member, an insertion device adapted to hold a portion of the first anchor, and a tensioning and crimping tool having an outer elongated member and an inner member movably disposed within the outer member;

inserting a portion of the elongated member into the insertion device;

interconnecting a portion of the first rigid anchor and the insertion device;

impelling the insertion device with interconnected first rigid anchor through the first and second cortical bone segments;

pivoting the first rigid anchor with respect to the insertion device to the anchor position;

sliding the second deformable anchor on the elongated member adjacent the proximal tissue segment;

threading the elongated member through the tensioning and crimping tool;

applying tension on the elongated member to urge the first rigid anchor toward the second deformable anchor thereby urging the first cortical bone segment toward the second cortical bone segment; and moving the inner member with respect to the outer member thereby deforming the deformable portion of the second deformable anchor and maintaining the tension applied to the elongated member.

19. The method of claim 18, wherein said insertion device is adapted to releasably engage the elongated member, further including applying tension to the elongated member after said interconnecting and releasably engaging the elongated member with the insertion device to thereby hold the first rigid anchor in alignment with the insertion device.

20. The method of claim 18, wherein the tensioning and crimping tool includes a cutting mechanism, further including operating the cutting mechanism to cut the elongated member adjacent the second deformable anchor.

21. The method of claim 20, wherein the cutting mechanism is disposed adjacent the second deformable anchor and cuts a portion of the second deformable anchor during said operating.

* * * * *